US008088818B2

(12) United States Patent
Kuo et al.

(10) Patent No.: US 8,088,818 B2
(45) Date of Patent: Jan. 3, 2012

(54) CATECHOL-BASED DERIVATIVES FOR TREATING OR PREVENTING DIABETICS

(75) Inventors: Yueh-Hsiung Kuo, Taipei (TW); Ming-Jai Su, Taipei (TW)

(73) Assignee: National Taiwan University, Taipei (TW)

( * ) Notice: Subject to any disclaimer, the term of this patent is extended or adjusted under 35 U.S.C. 154(b) by 27 days.

(21) Appl. No.: 12/368,167

(22) Filed: Feb. 9, 2009

(65) Prior Publication Data

US 2009/0143397 A1    Jun. 4, 2009

Related U.S. Application Data

(63) Continuation-in-part of application No. PCT/CN2006/001991, filed on Aug. 7, 2006.

(51) Int. Cl.
*A01N 43/36* (2006.01)
*A61K 31/40* (2006.01)

(52) U.S. Cl. ..................................................... 514/423
(58) Field of Classification Search .................. 514/423; 548/540
See application file for complete search history.

(56) References Cited

U.S. PATENT DOCUMENTS 5,232,923 A * 8/1993 Fukazawa et al. ......... 514/237.5

OTHER PUBLICATIONS

Hsu, et al., Planta Med, 66(3), 228-230 (2000).*
Fuliang, et al., Pharmacol. Res. 51(2), 147-152 (2005).*
Matsui, et al., Biol. Pharm. Bull., 27(11), 1797-1803 (2004).*
Tolan et al., Phytother Res, 18(1), 95-96 (2004).*
Mahesh, et al., Therapie, 59(6), 639-644 (2004).*
Wang, et al., Chemical Structure-physiological Activity Relationship in Cinnamamides and Their Analogs. III. Relationship between Chemical Structure and Anticonvulsant Action, Beijing Yixueyuan Xuebao, 14(1), 65-70 (1982).*

* cited by examiner

*Primary Examiner* — Andrew D Kosar
*Assistant Examiner* — Erich A Leeser
(74) *Attorney, Agent, or Firm* — Osha • Liang LLP

(57) ABSTRACT

The present invention provides a catechol-based derivative and a pharmaceutical acceptable salt therefrom and a solvate therefrom. A pharmaceutical composition for preventing or treating diabetics and ischemics, comprising a catechol-based derivative of formula (I) and at least one selected from the group consisting of a pharmaceutical excipient, a diluent and a carrier.

(I)

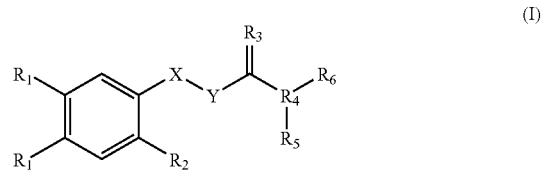

2 Claims, 3 Drawing Sheets

CATECHOL-BASED DERIVATIVES FOR TREATING OR PREVENTING DIABETICS

FIELD OF THE INVENTION

The present invention relates to a compound having an antioxidant activity and the ability to prevent and treat diabetics or ischemias and the preparation thereof. More particularly, the present invention relates to a catechol-based derivative and the preparation thereof.

BACKGROUND OF THE INVENTION

There are currently 15.7 million people or 5.9% of the population in the United States who suffer from diabetes mellitus. Each day approximately 2,200 people are diagnosed with diabetes and roughly 798,000 people will be diagnosed this year. Diabetes is the seventh leading cause of death (sixth-leading cause of death by disease) in the United States.

Diabetes mellitus, more commonly known as diabetes, is a disease in which body does not produce and/or properly use insulin, a hormone that aids the body in converting sugars and other foods into energy. In a non-diabetic individual, insulin is produced in the pancreas at the islets of Langerhans in response to an increase in glucose in the gut and/or blood. Insulin then acts in conjunction with the liver to control glucose metabolism in the body. While diabetes is typically considered as a blood-sugar disease, diabetes may result in numerous life-threatening complications. For example, diabetes may lead to various microvascular diseases, such as coronary artery heart disease, retinopathy, nephropathy, and neuropathy. Diabetes mellitus is a medical disorder characterized by varying or persistent hyperglycemia (high blood sugar levels) resulting from the defective secretion or action of insulin. Nowadays, the complication of diabetes can be controlled by maintaining the glucose level in advance to prevent or defer the development of illness. Therefore, it is worth to develop a powerful anti-diabetic drug for controlling the patient's glucose level within a normal range.

There are several types of diabetes mellitus, which is classified based on their aetiology:

1. Type 1: Insulin dependent diabetes mellitus (IDDM), commonly referred to as Type 1 diabetes, is an auto-immune disease. Type 1 diabetes occurs when body's immune system attacks and destroys beta cells in the islets of Langerhans in the pancreas. Beta cells normally produce insulin. If the beta cells are destroyed, no insulin can be produced, and glucose stays in the blood, where high level of glucose can cause serious damage to all organ systems in the body. Type 1 diabetes may affect as many as 1 million people in the United States.

2. Type 2: Non-insulin dependent diabetes mellitus (NIDDM), commonly referred to as Type 2 diabetes, is a metabolic disorder resulting from body's inability to produce sufficient insulin or properly use the insulin produced. Type 2 diabetes is characterized by peripheral insulin resistance with an insulin-secretory defect that varies in severity. Roughly 90 percent of all diabetic individuals in the United States suffer from Type 2 diabetes, which is usually associated with obesity and a sedentary lifestyle.

3. Specific type: The aetiology of this type of diabetes, which is a secondary diabetes, can be traced to other diseases such as Hemochromatosis and Cushing's syndrome.

4. Gestational Diabetes

Under normal conditions, patients suffering from type 1 diabetes must take or inject insulin for body's necessary functions. This means undergoing multiple injections daily, or having insulin delivered through an insulin pump, and testing their blood sugar by pricking their fingers for blood about six or more times a day. Patients suffering from Type 2 diabetes often control their glucose level in the blood by taking anti-diabetic drug orally. The present oral anti-diabetic drugs are classified into five types.

1. Sulfonylurea-based derivative: This type of medicine binds to a sulfonylurea receptor existing in an ATP-dependent $K^+$ channel on the cell membrane of pancreatic beta cells, resulting in the inhibition of the $K_{ATP}$ channel and depolarization of membrane potential. As a result, voltage-gated $Ca^{2+}$ channels are opened, and the rise in intracellular calcium leads to increased secretion of (pro)insulin.

2. Biguanide-based derivative: Metformin is the most common drug in this class. Metformin stimulates a hepatic enzyme, AMP-activated protein kinase (AMPK), which enhances GLUT4 translocation to increase glucose uptake and utilization. In addition, Metformin increases the sensitivity of muscle cells to insulin, increasing muscle cell's ability to store glucose.

3. Thiazolidinedione-based derivatives: this class of drugs binds to PPARs (peroxisome proliferator-activated receptors), a group of receptor molecules inside the cell nucleus, specifically PPARγ (gamma). This kind of drugs could enhance the insulin activity in the muscles and fatty tissues, as well as reduce the glucose synthesis in the liver and promote the conversion of blood sugar into the fatty acids.

4. α-glucosidase inhibitor: This kind of drug is capable of inhibiting the activities of both pancreasα-amylase and intestinal α-glucosidase, so that the degradation of starch and carbohydrate is inhibited. Therefore, the glucose absorption into the intestine is reduced.

5. Meglitinide-based derivatives: This kind of drugs binds to 36 kDa receptor existing in an ATP-dependent $K^+$ channel on the cell membrane of pancreatic beta cells, leading to the inhibition of the ATP-dependent potassium channels in beta cells and opening of the calcium channels. The resulting calcium influx causes the cells to secrete insulin. These drugs act quickly when taken orally. Thus, it is recommended that these drugs be taken before meals to help control the rise in blood sugar levels after meals.

In addition, earlier studies showed that several catechol-containing natural products, such as caffeic acid (Hsu F L, Chen Y C, Cheng J T et al., *Planta Med*, 66(3), 228-230, 2000), extracts of propolis from north China (Fuliang H U, Hepburn H R et al., *Pharmacol Res*, 51(2), 147-152, 2005), extracts of propolis from Brazil (Matsui T, Ebuchi S, Fujise T et al, *Biol Pharm Bull*, 27(11), 1797-1803, 2004), capsaicin (Tolan I, Ragoobirsingh D, Morrison E Y, *Phytother Res*, 18(1), 95-96, 2004), curcumin (Mahesh T, Sri Balasubashini M M, Therapie 2004, 59(6): 639-644), and the like, are effective in lowering blood sugar.

Diabetes is often associated with cardiovascular diseases, particularly, ischaemic heart disease, which is a disease characterized by reducing blood supply to the heart. Ischaemic hear disease often results in acute myocardial infarction (AMI), a congestive heart failure, arrhythmia, and sudden death. It is the most common cause of morbidity and mortality in most industrial countries. According to statistics published by the United State government in 2001, death resulting from ischaemic heart disease accounts for 20% of total death numbers (approximately 60 million deaths per year) (Myerburg R J., *Cardiovasc Electrophysiol.*, 12, 369-381, 2001), wherein the majority of the deaths is caused by sudden death of people falling ill for first time. In addition, it is estimated that there are approximately 110 million Americans suffering from AMI in 2001, including new cases and recurrence cases.

Many patients noted above develop subsequent complications, which cause heart failures and deaths. In recent years, the increase in aging population and other common complications, such as the obesity and the diabetes, puts a greater burden on public health budgets for ischaemic heart disease. Therefore, how to effectively minimize ischaemia and reduce injuries associated with reperfusion of ischaemic hearts has become an important medical issue.

Two key factors impact the outcome of treating ischaemic heart diseases. One is to take actions to prevent or minimize cardiac arrhythmia. Most patients suffering from acute myocardial infarction die from arrhythmia; some of these patients may survive because of spontaneous recovery of the heart rhythm or after a cardiopulmonary resuscitation (CPR). However, the success in the treatment for cardiac arrest has been dismal in the past thirty years.

Another factor is to minimize the size of myocardial infarction due to ischaemia or ischaemia-reperfusion. The degree of recovery depends on the extent of injury of the cardiac muscle after ischaemia or ischaemia-reperfusion. The standard protocols for treating acute myocardial infarction include giving patients thrombolytic agent or performing percutaneous transluminal coronary angioplasty (PTCA). These treatments could immediately recover the blood flow to the heart. Although such treatments are helpful in preventing further deterioration of the ischaemic cardiac muscles, they may lead to complications. Particularly, in high risk populations, surgery may lead to prolonged contractile dysfunction (or stunning), perioperative myocardial infarction, and cardiac failure. Therefore, there still exists a need for novel auxiliary treatments to be used in conjunction with the perfusion therapy to prevent injuries to the cardiac muscle caused by ischaemia or ischaemia-reperfusion.

The present invention provides a series of catechol-based derivatives, which promotes blood flow in the coronary artery, suggesting that they are capable of preventing or treating injuries of the cardiac muscles caused by ischaemia or ischaemia-reperfusion. Embodiments of the present invention not only solves the problems described above, but also is easy to implement.

SUMMARY OF THE INVENTION

In order to overcome the drawbacks in the prior art, the present invention provides a novel catechol-based derivative, which includes one selected from the group consisting of a compound of a formula (I), a pharmaceutical acceptable salt thereof, and a solvate thereof,

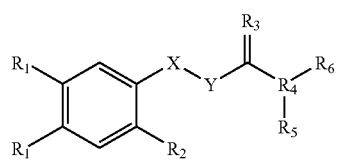

(I)

wherein $R_1$ and $R_2$ are independently selected from the group consisting of H, —OR, —NO$_2$, —NH$_2$, and a halogen; R in the —OR is one selected from the group consisting of H, $(C_1-C_6)$alkyl, $(CH_2)_n$Ph, SO3$^-$, and Ar; $R_3$ is one of O and S; $R_4$ is N; X and Y are selected from the group consisting of alkyl, alkenyl, alkynyl, and —OCH$_2$—; $R_5$ is one selected from the group consisting of H, $(C_1-C_{15})$alkyl, $(CH_2)_n$Ar and Ar; $R_6$ is one of H and $(C_1-C_6)$alkyl and n is an integer from 1~3.

Preferably, the two $R_1$ substituents on the benzene ring form the following structure:

(a)

Preferably, $R_5$-$R_4$-$R_6$ forms a cyclic structure selected from the group consisting of:

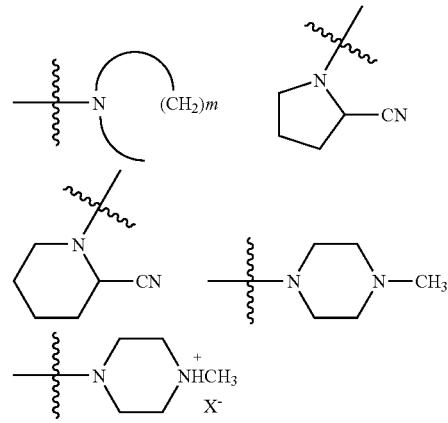

wherein m is an integer from 2-6.

Preferably, Ar is one selected from the group consisting of

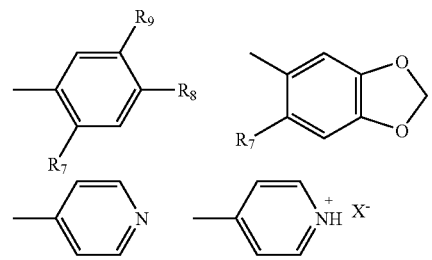

and a heteroaryl group;
wherein $R_7$, $R_8$, $R_9$ are selected from the group consisting of H, —OH, —OCH$_3$, —NO$_2$, —NH$_2$, —NH$_3^+$, and a halogen; and X— represents an organic base or an inorganic base.

In accordance with another aspect of the present invention, a pharmaceutical composition for preventing or treating diabetics, comprising a catechol-based derivative described above and at least one selected from the group consisting of a pharmaceutical excipient, a diluent and a carrier is provided.

Preferably, the pharmaceutical composition is used for preventing and treating damages of kidney, brain and heart resulting from an obstruction of a blood vessel (i.e., ischemia).

In accordance with further aspect of the present invention, a pharmaceutical composition for preventing or treating ischemia, comprising a catechol-based derivative described above and one selected from the group consisting of a pharmaceutical excipient, a diluent and a carrier.

Preferably, the pharmaceutical composition is used for preventing and treating damages of kidney, brain and heart resulting from an obstruction of a blood vessel (i.e., ischemia).

The above aspects and advantages of the present invention will become apparent to those ordinarily skilled in the art after reviewing the following detailed descriptions and accompanying drawings, in which:

DETAILED DESCRIPTION OF THE PREFERRED EMBODIMENT

Figure 1:
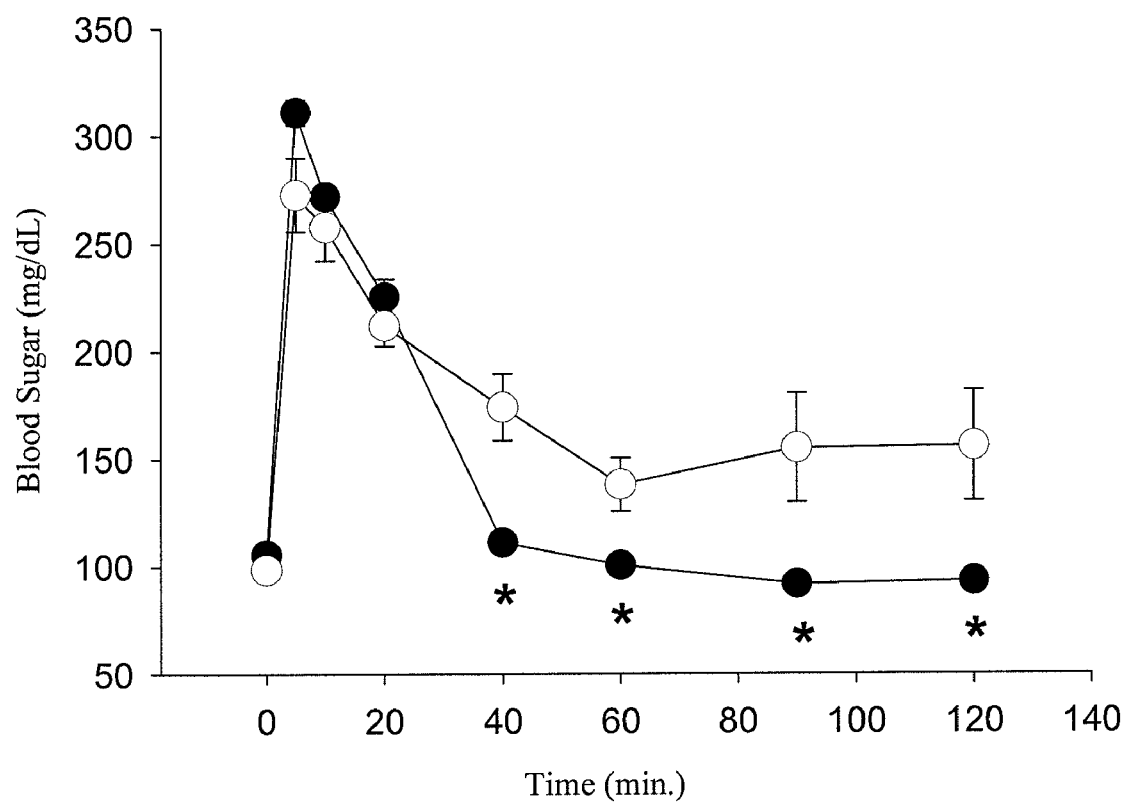
FIG. 1 shows results from intravenous glucose tolerance test (IGTT) in response to the treatment with compound 370G.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

The present invention discloses a series of catechol-based derivatives. The catechol-based derivatives having the formula (I) may be prepared by reacting caffeic acids with alcohols in the presence of an inorganic acid as a catalyst, or alternatively by refluxing the compound containing $RNH_2$ functional groups with the acyl chloride formed by reacting 3(3,4-methylendioxyphenyl)-propenoic acid with dichloromethane ($CH_2Cl_2$) and thionyl chloride ($SOCl_2$). An alternative synthesis of the catechol-based derivatives is to mix N,N-dimethylformamide (DMF) and BOP (Benzotrizoly-N-hydroxy trisdimethylamono) phosphonium hexafluororophosphate) in dichloromethane, followed by refluxing the resultant solution with an amino compound, $RNH_2$.

Substitution of Functional Group

Reactants for the present invention could be prepared by esterification to convert the original functional group into an ester group. For example, methyl ester may be prepared by refluxing a mixture of p-toluenesulfonic acid (TsOH) and 2,2-dimethoxypropane in methanol. If another ester is desire, it cold be prepared by refluxing the mixture of p-toluenesulfonic acid (TsOH) and 2,2-dimethoxypropane in a desire alcohol. The resultant ester may be dissolved in tetrahydrofuran (THF) and reduced with $LiAlH_4$ to the corresponding alcohol. The resultant alcohol may be dissolved in tetrahydrofuran (THF), deprotonated with sodium hydride (NaH), and reacted with an alkyl bromide (RBr) to produce an ether compound.

Scheme 1 illustrates such a process. Methyl ester is prepared by putting caffeic acid (compound (1) in Scheme 1) in a glass flask, followed by the addition of TsOH, 2,2-dimethoxypropane and the methanol. The resultant solution is heated to reflux to produce methyl ester of caffeic acid. Other esters (other than methyl esters) may be prepared by refluxing the mixture of compound 1 and TsOH in a desired alcohol as a solvent. After the reaction, the solvent is removed and the residue poured into water. The ester is extracted with ethyl acetate. The extract is neutralized and purified with a column chromatography to afford ester derivative (A). Various examples of esters (A) thus prepared are shown in Table 1.

The ester derivative (A) is dissolved in methanol and hydrogenated in the presence Pd—C as a catalyst to afford a saturated ester. After hydrogenation, the catalyst was removed by filtration and washed with methanol to produce the corresponding saturated ester derivative (B). Various ester (B) thus prepared are shown in Table 2.

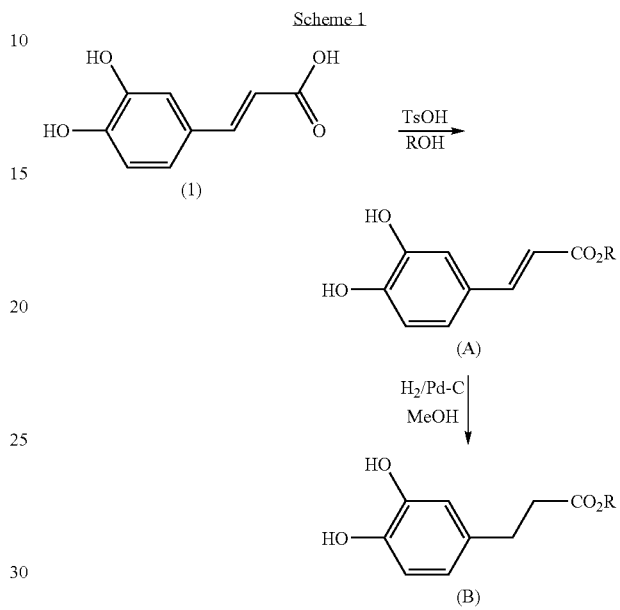

Referring to Scheme 2, under nitrogen atmosphere, a suspension of 3,4-Methylenedioxycinnmamic acid (30) in dry $CH_2Cl_2$ is treated with thionyl chloride and heated to reflux. After removal of the solvent in vacuum, an acyl chloride residue is obtained. A solution containing an amine ($RNH_2$) and triethylamine is added to the acyl chloride residue and stirred. After removal of the solvent, the resultant residue is extracted with ethyl acetate. The organic extracts are combined, filtered, and evaporated. The residue is purified by column chromatography to afford derivative (C). Examples of derivative (C) thus prepared are shown in Table 3.

In a two-neck flask, a derivative (C) is dissolved in $CH_2Cl_2$, reacted with $BBr_3$ at approximately −30° C., and then the reaction is terminated with the addition of ice water. The resultant solution is extracted with $CH_2Cl_2$. The organic extracts are combined, dried, filtered, and evaporated. The residue is purified with column chromatography to produce derivative (D). Examples of derivative (D) are shown in Table 4.

Dissolve the type-D derivatives in the methanol, which saturates with hydrogen gases in the presence of Pd—C as a catalyst to give a reactant, followed by filtering the catalyst and washing with methanol to obtain a corresponding type-E derivative. Dissolve the type-E derivatives in a two-neck bottle containing the pyridine, and react the resultant solution with $Ac_2O$ at the room temperature for overnight, and then the reaction is terminated with the addition of ice water. The resultant solution is further extracted by $CH_2Cl_2$, wherein the organic phase is collected to remove water, to be filtered, to be condensed and perform a column chromatography. Accordingly, type-H derivatives could be obtained, please referring to Table 5.

Scheme 2

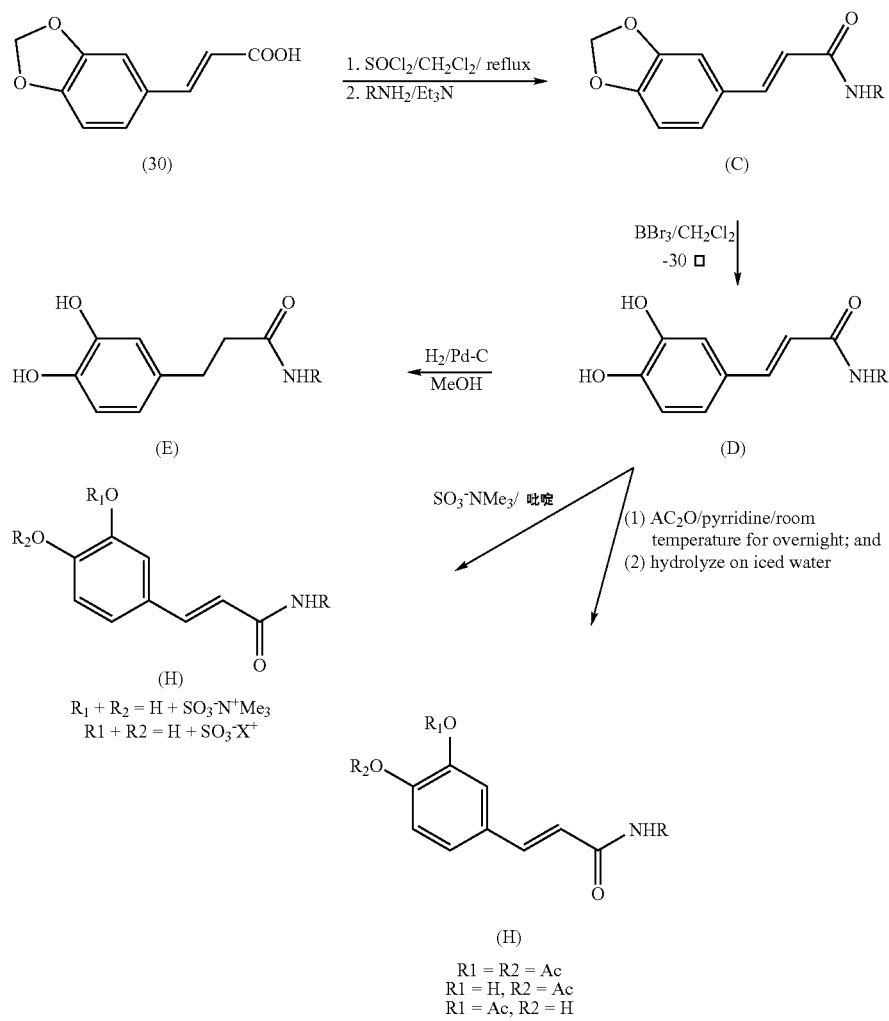

Put 10 g of the compound 30 into a reaction bottle, followed by adding TsOH and 2,2'-dimethyloxypropane dissolved in the methanol solution thereinto. Reflux the resultant solution, and then remove the solvent therefrom, followed by being extracted by the ethyl acetate. Perform a column chromatography of the resultant extract to obtain a product. Dissolve the product in methanol, which saturates with hydrogen gases in the presence of Pd—C as the catalyst. After the reaction, remove the catalyst and wash the methanol to obtain the corresponding compound 56.

Please refer to Scheme 3. Put LiAlH₄ into a reaction bottle, and then further add the compound 56 and tetrahydrofuran thereinto, followed by stirring at the room temperature. Reduce the pressure to remove the solvent and then adjust the pH value. Extract the resultant solution by the ethyl ester, wherein the organic phase is condensed to obtain the product 57. The product 57 is stirred in the treatment of NaH and THF for half an hour, followed by adding RBr to react. Reduce the pressure to remove the solvent, followed by being extracted by the ether, wherein the organic phase is collected to obtain type-F derivatives, please referring to Table 7. Dissolve the type-F derivatives in CH₂Cl₂, and react with BBr₃ at −30° C., followed by being extracted by CH₂Cl₂, collecting the organic phase to remove water, filtering, condensing and performing a column chromatography. Accordingly, type-G derivatives could be obtained, please referring to Table 8.

Scheme 3

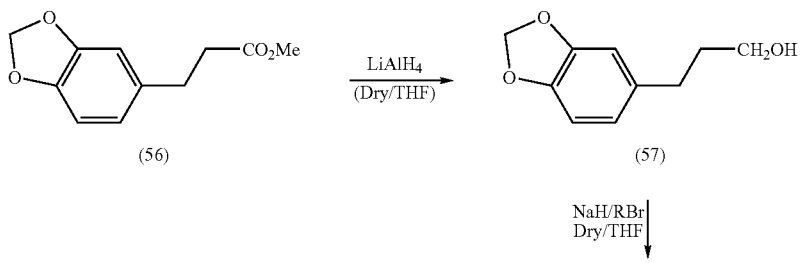

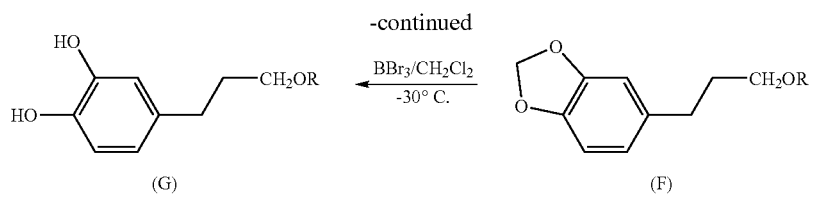

Please refer to Scheme 4. Dissolve the caffeic acid in N,N-dimethylformamide and triethylamine, and then react with BOP and $CH_2Cl_2$ to obtain the corresponding compound.

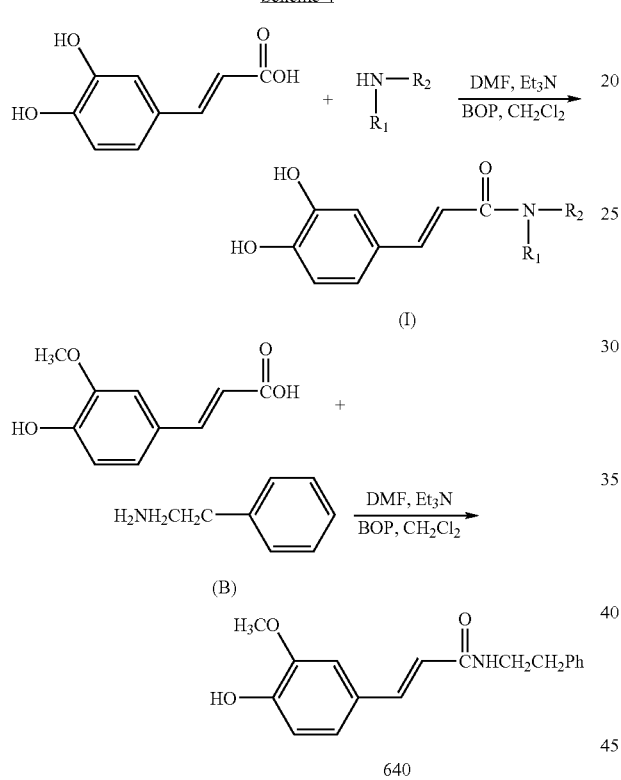

Scheme 4

Example 1

Preparation of the Type-A Derivatives

Put a 10 g caffeic acid (1) in a reaction bottle, and add 1 g TsOH and 3 ml 2,2-dimethoxypropane and 10 ml methanol thereinto, followed by refluxing for 6 hours. After the refluxation, remove the solvent and pour the resultant solution into 100 ml water, followed by being extracted by the ethyl acetate for three times, neutralizing with 3% $NaHCO_3$, and finally performing a column chromatography. Therefore, the product, methyl caffeate (the compound 2) is obtained with 98% yield.

Correspondingly, select the desired alcohol as the replacing group to substitute methanol, so as to synthesize the respective compounds 3-15 of the type-A derivatives.

TABLE 1

Type-A derivatives

| Compound | R | Compound | R | Compound | R |
|---|---|---|---|---|---|
| 2 | $CH_3$ | 3 | $C_2H_5$ | 4 | $C_3H_7$ |
| 5 | $C_4H_9$ | 6 | $C_5H_{11}$ | 7 | $C_6H_{13}$ |
| 8 | $C_7H_{15}$ | 9 | $C_8H_{17}$ | 10 | $C_9H_{19}$ |
| 11 | $C_{10}H_{21}$ | 12 | $C_{11}H_{23}$ | 13 | —$CH_2Ph$ |
| 14 | —$(CH_2)_2Ph$ | 15 | —$(CH_2)_3Ph$ | | |

Example 2

Preparation of Type-B Derivatives

Dissolve 200 g methyl caffeate (2) in 10 ml methanol, which saturates with hydrogen gases in the presence of 20 mg Pd—C, and react for six hours, followed by filtering the catalyst and washing with methanol to obtain the corresponding compound 16 as shown in Table 2.

Correspondingly, select the respective compounds 3-15 to substitute the original methyl caffeate (2) to react, so as to synthesize the respective compounds 17-29 of the type-B derivatives as shown in Table 2 could be obtained.

TABLE 2

Type-B derivatives

| Compound | R | Compound | R | Compound | R |
|---|---|---|---|---|---|
| 16 | $CH_3$ | 17 | $C_2H_5$ | 18 | $C_3H_7$ |
| 19 | $C_4H_9$ | 20 | $C_5H_{11}$ | 21 | $C_6H_{13}$ |
| 22 | $C_7H_{15}$ | 23 | $C_8H_{17}$ | 24 | $C_9H_{19}$ |
| 25 | $C_{10}H_{21}$ | 26 | $C_{11}H_{23}$ | 27 | —$CH_2Ph$ |
| 28 | —$(CH_2)_2Ph$ | 29 | —$(CH_2)_3Ph$ | | |

Example 3

Preparation of Type-C Derivatives

In the presence of nitrogen gases, dissolve a suspension of 10 g 3,4-Methylenedioxycinnmamic acid (30) in 10 ml $CH_2Cl_2$, and then add 2 mol thionyl chloride thereinto, followed by refluxing for three hours to remove $CH_2Cl_2$ and thionyl chloride therefrom. Add a 10 ml triethylamine solution containing 3 nmol $C_4H_9NH_2$ under the iced bath and stir the solution for overnight. Remove the triethylamine solution and extract the resulting solution with the 50 ml ethyl ester, wherein the organic phase is collected to remove water by $MgSO_4$, to be filtered, to be condensed and perform a column chromatography. Therefore, the type-C derivatives as shown in Table 3 could be obtained.

Correspondingly, select the desired amine compound to substitute the $C_4H_9NH_2$, so as to synthesize the respective compounds 32-38 of the type-C derivatives with 78~85% yields.

TABLE 3

Type-C derivatives

| Compound | R | Compound | R | Compound | R |
|---|---|---|---|---|---|
| 31 | $C_4H_9$ | 32 | $C_5H_{11}$ | 33 | $C_6H_{13}$ |
| 34 | $C_7H_{15}$ | 35 | $C_8H_{17}$ | 36 | —$CH_2Ph$ |
| 37 | —$(CH_2)_2Ph$ | 38 | —$(CH_2)_3Ph$ | | |

Example 4

Preparation of Type-D Derivatives (I)

In the presence of nitrogen gases, dissolve a 1.0 g N-butyl 3,4-methylenedioxycinnamamide of the type-C derivative into a two-neck bottle containing 10 ml $CH_2Cl_2$. Add 1.2 mol $BBr_3$ into the bottle at −30□ to react for four hours. After the reaction is finished, further add 50 ml, 3% $NaHCO_3$ thereinto. Extract the resulting solution by $CH_2Cl_2$ three times, and concentrate the organic phase. Remove water from the above organic phase by $MgSO_4$, followed by performing a filtration, a condensation, and a column chromatography. Therefore, the compound 39 as shown in Table 4 could be obtained.

Correspondingly, select the respective compound 32~38 to substitute the original compound 31, so as to synthesize the respective compounds 40-46 of the type-D derivatives with 78~85% yields.

TABLE 4

Type-D derivatives

| Compound | R | Compound | R |
|---|---|---|---|
| 39 | $C_4H_9$ | 40 | $C_5H_{11}$ |
| 41 | $C_6H_{13}$ | 42 | $C_7H_{15}$ |
| 43 | $C_8H_{17}$ | 44 | $CH_2Ph$ |
| 45(370G) | —$(CH_2)_2Ph$ | 46 | —$(CH_2)_3Ph$ |
| 638A | —$(CH_2)_2Ph(OCH_3)_2$ | 638B | —$(CH_2)_2Php-Br$ |
| 638C | —$(CH_2)_2Php-OH$ | 638D | —$CH_2Ph-p-OCH_3$ |
| 638E | —$CH_2Ph$ | 638F | -Ph-p-$OCH_3$ |
| 638G | -Ph-p-Br | 638H | Ph p-OH |
| 638I | —$CH_2Ph-m-F$ | | |

Example 5

Preparation of Type-D Derivatives (II)

Dissolve a 100 mg caffeic acid in 1 ml N,N-dimethylformamide and 1 mol, 0.08 ml triethylamine in a two-neck bottle, and then add into 1.2 mol, 5 ml $CH_2Cl_2$ containing the desired amine compound ($RNH_2$) and 1.2 mol BOP to react for 30 minutes at 0□, followed by reacting for 2 hours at the room temperature. After the reaction is finished, remove $CH_2Cl_2$. The resulting solution is then added into 50 ml water, which is extracted by the ethyl ester. Collect the organic phase, and wash the organic phase with 1 mol HCL, 1 mol $NaHCO_3$ and water, wherein the organic phase is further recollected, followed by removing water therefrom by $MgSO_4$, performing a filtration, a condensation, and a column chromatography. Therefore, the type-D derivatives as shown in Table 5 could be obtained with 65~85% yield (such as 638A-I). If selecting a ferrulic acid and 2-phenylethanamide to substitute the mentioned compounds, the compound 640 could be obtained.

Example 6

Preparation of Type-E Derivatives

Dissolve 200 mg N-alkyl caffeamide in 10 ml methanol, which saturates with hydrogen gases in the presence of 20 mg Pd—C, and react for six hours, followed by filtering the catalyst and washing with methanol to obtain a corresponding compound of the type-E derivatives (the product is 47-54) as shown in Table 5.

TABLE 5

Type-E derivatives

| Compound | R | Compound | R | Compound | R |
|---|---|---|---|---|---|
| 47 | $C_4H_9$ | 48 | $C_5H_{11}$ | 49 | $C_6H_{13}$ |
| 50 | $C_7H_{15}$ | 51 | $C_8H_{17}$ | 52 | —$CH_2Ph$ |
| 53 | —$(CH_2)_2Ph$ | 54 | —$(CH_2)_3Ph$ | | |

Example 7

Preparation of the Respective Compound 56 and 57

Put a 10 g the compound 30 in a reaction bottle, and add 1 g TsOH, 3 ml 2,2-dimethoxypropane and 100 ml methanol thereinto, followed by refluxing for 6 hours. Remove the solvent, and pour the resulting solution into 100 ml water. Then, extract the resultant solution by the ethyl acetate for three times and washed with 3% $NaHCO_3$, followed by performing a column chromatography to obtain the compound A. Dissolve 5 g of the compound A in 20 ml methanol, which saturates with hydrogen gases in the presence of 20 mg Pd—C, and react for six hours, followed by filtering the catalyst and washing with methanol to obtain the corresponding compound 56.

Put $LiAlH_4$ in a reaction bottle, and then add the compound 56 (4 g) and 10 ml tetrahydrofuran thereinto, followed by stirring at the room temperature for the reaction. Add an ether to terminate the reaction. Reduce the pressure to remove the solvent from the resultant solution, and then add 100 ml, 3N $H_2SO_4$ thereinto. Extract the resulting solution by the ethyl ester three times, wherein the organic phase is condensed to obtain the product 57.

Example 8

Preparation of the Compound 58

At the room temperature, react the compound 57 with 300 g NaH and 10 ml THF by stirring for an hour. Add 3 mol $CH_3I$ into the resultant solution to react, followed by reducing the pressure to remove the solvent, pouring into water and successively being extracted by ether. The resultant organic phase is collected to obtain the compound 58.

Example 9

Preparation of Type-F Derivatives

According to the preparation of the example 8, the compound 57 serves as a starting material to react respectively with $C_2H_5Br$, $C_3H_7Br$, and $C_4H_9Br$ containing an alkyl bromide to substitute $CH_3I$, so as to synthesize the respective compounds 59-61 of the type-F derivatives as shown in Table 7.

| Type-F derivatives |||||||
| --- | --- | --- | --- | --- | --- | --- |
| Compound | R | Compound | R | Compound | R | Compound | R |
| 58 | $CH_3$ | 59 | $C_2H_5$ | 60 | $C_3H_7$ | 61 | $C_4H_9$ |

Example 10

Preparation of Type-G Derivatives

According to the preparation of example 4, substitute the type-F derivatives to the type-C derivatives, so as to synthesize the type-G derivatives with 70-75% yield as shown in Table 8.

TABLE 8

| Type-G derivatives ||||||
| --- | --- | --- | --- | --- | --- |
| Compound | R | Compound | R | Compound | R |
| 62 | $CH_3$ | 63 | $C_2H_5$ | 64 | $C_3H_7$ |
| 65 | $C_4H_9$ | | | | |

Example 11

Preparation of Type-H Derivatives

In the presence of nitrogen gases, put 50 mg, 0.19 mmol of the compound 370G (45) in a two-neck bottle and dissolve in a 10 ml Pyridine, followed by adding $Ac_2O$ therein to react for overnight, and adding the iced water thereinto. Extract the resulting solution by the ethyl ester, and collect the organic phase, remove water therefrom by $MgSO_4$, performing a filtration, and a condensation. Therefore, 50 mg, 0.17 mmol of the pure compound 639B and the mixed compound 639C could be obtained with 88% yields as shown in Table 6.

| Type-H derivatives ||||
| --- | --- | --- | --- |
| Compound | R | $R_1$ | $R_2$ |
| 639A | —$(CH_2)_2$Ph | $CH_3$ | $CH_3$ |
| 639B | —$(CH_2)_2$Ph | Ac | Ac |
| 639C | —$(CH_2)_2$Ph | | Ac, H |
| 640 | —$(CH_2)_2$Ph | $CH_3$ | H |

Example 12

Preparation of Type-H Derivatives

Dissolve a mixture of 370 G (45) and $CH_3I$ in acetone and add $K_2CO_3$ to reflux, so as to purify the compound 639A.

Example 13

Preparation of Type-I Derivatives

According to the preparation of the example 5, react the caffeic acid with the respective N-methyl-2-phenylethanamine, the N-methyl-2-phenylmethamine, the pyrrolidine, the piperidine and the N-methyl-1,4-diazacyclohexane to obtain the respective compound 642A, 642B, 642C and 642D as shown in Table 9.

TABLE 9

| Type-I derivatives ||||
| --- | --- | --- | --- |
| Compound | $R_1$ | $R_2$ | | | $R_1 + R_2$ |
| 642A | $CH_3$ | $CH_2$Ph | 642C | —$(CH_2)_4$— |
| 642B | $CH_3$ | $CH_2CH_2$Ph | 642D | —$(CH_2)_5$— |

The physical properties of the respective example compounds of the present invention are shown as follows.

Compound 2: methyl caffeate
Mp: 160-162 □
$IRv_{max}$ ($cm^{-1}$): 3485, 3306, 1673, 1631, 1598, 1528, 1275, 1179, 975, 848
MS m/z (%): 194 ($M^+$, 100), 163 (63), 145 (11), 134 (18)
$^1$H-NMR ($CDCl_3$): δ3.78 (3H, s), 5.80, 5.91 (each 1H, br s, —OH), 6.24, 7.56 (each 1H, d, J=15.9 Hz), 6.85 (1H, d, J=8.2 Hz), 6.98 (1H, dd, J=8.2, 2.0 Hz), 7.06 (1H, d, J=2.0 Hz).

Compound 3
Mp: 118-120□
$IRv_{max}$ ($cm^{-1}$): 3500, 3400, 1652, 1630, 1597, 1279, 1187, 973, 850, 811
MS m/z (%): 208 ($M^+$, 100), 180 (20), 163 (62), 145 (20), 136 (33)
$^1$H-NMR ($CDCl_3$): δ 1.26 (3H, t, J=7.1 Hz), 4.17 (2H, q, J=7.1 Hz), 6.25, 7.53 (each 1H, d, J=15.9 Hz), 6.85 (1H, d, J=7.2 Hz), 7.02 (1H, dd, J=7.2, 2.1 Hz), 7.14 (1H, d, J=2.1 Hz), 8.30 (2H, br s, —OH).

Compound 4
Mp: 124-126□
$IRv_{max}$ ($cm^{-1}$): 3480, 3345, 1684, 1628, 1600, 1528, 1275, 1186, 975, 851, 811
MS m/z (%): 222 ($M^+$, 100), 180 (57), 163 (78), 145 (13), 138 (22), 136 (21)
$^1$H-NMR ($CD_3COCD_3$): δ 0.84 (3H, t, J=7.2 Hz), 1.66 (2H, sext, J=7.2 Hz), 4.08 (2H, t, J=7.2 Hz), 6.28, 7.53 (each 1H, d, J=15.9 Hz), 6.86 (1H, d, J=7.1 Hz), 7.03 (1H, dd, J=7.1, 2.0 Hz), 7.15 (1H, d, J=2.0 Hz), 8.28 (2H, br s, —OH).

Compound 5
Mp: 106-108□
$IRv_{max}$ ($cm^{-1}$): 3479, 3337, 1678, 1632, 1599, 1529, 1276, 1183, 1105, 973, 783, 718
MS m/z (%): 236 ($M^+$, 83), 180 (100), 163 (73), 145 (12), 136 (25), 134 (23)
$^1$H-NMR ($CD^3COCD^3$): δ 0.93 (3H, t, J=7.2 Hz), 1.40 (2H, sext, J=7.2 Hz), 1.63 (2H, quin, J=7.2 Hz), 4.13 (2H, t, J=7.2 Hz), 6.26, 7.52 (each 1H, d, J=15.9 Hz), 6.85 (1H, d, J=7.7 Hz), 7.03 (1H, dd, J=7.7, 2.1 Hz), 7.14 (1H, d, J=2.1 Hz).

Compound 6
Mp: 140-142□
$IRv_{max}$ ($cm^{-1}$): 3486, 3332, 1678, 1632, 1598, 1529, 1276, 1181, 974, 851, 783
MS m/z (%): 250 ($M^+$, 69), 180 (100), 163 (62), 145 (11), 136 (16), 134 (18)
$^1$H-NMR ($CD_3COCD_3$): δ 0.88 (3H, t, J=6.7 Hz), 1.36 (4H, m), 1.64 (2H, quin, J=7.2 Hz), 4.12 (2H, t, J=7.2 Hz), 6.27, 7.52 (each 1H, d, J=15.9 Hz), 6.85 (1H, d, J=8.2 Hz), 7.04 (1H, dd, J=8.2, 2.2 Hz), 7.15 (1H, d, J=2.2 Hz), 8.30 (2H, br s, —OH).

Compound 7

Mp: 115-117☐

IRν$_{max}$ (cm$^{-1}$): 3483, 3333, 1679, 1632, 1598, 1529, 1275, 1182, 1104, 973, 812

MS m/z (%): 264 (M$^+$, 43), 180 (100), 163 (57), 145 (13), 136 (20), 134 (19)

$^1$H-NMR (CD$_3$COCD$_3$): δ 0.88 (3H, t, J=6.7 Hz), 1.36 (6H, m), 1.64 (2H, quin, J=6.7 Hz), 4.13 (2H, t, J=6.7 Hz), 6.26, 7.52 (each 1H, d, J=15.9 Hz), 6.85 (1H, d, J=8.2 Hz), 7.03 (1H, dd, J=8.2, 2.0 Hz), 7.14 (1H, d, J=2.0 Hz), 8.15 (2H, br s, —OH).

Compound 8

Mp: 105-106 ☐

IRν$_{max}$ (cm$^{-1}$): 3486, 3337, 1677, 1630, 1598, 1529, 1276, 1181, 1057, 974

MS m/z (%): 278 (M$^+$, 25), 180 (100), 163 (49), 145 (8), 136 (22), 134 (19), 89 (22)

$^1$H-NMR (CD$_3$COCD$_3$): δ 0.88 (3H, t, J=6.7 Hz), 1.36 (8H, m), 1.66 (2H, quin, J=6.7 Hz), 4.13 (2H, t, J=6.7 Hz), 6.27, 7.52 (each 1H, d, J=15.9 Hz), 6.85 (1H, d, J=8.1 Hz), 7.02 (1H, dd, J=8.1, 2.0 Hz), 7.15 (1H, d, J=2.0 Hz), 8.23 (2H, br s, —OH).

Compound 9

Mp: 98-100 ☐

IRν$_{max}$ (cm$^{-1}$): 3488, 3340, 1675, 1630, 1274, 1181, 972, 812

MS m/z (%): 292 (M$^+$, 27), 180 (100), 163 (47), 145 (8), 136 (18), 134 (12), 89 (13)

$^1$H-NMR (CD$_3$COCD$_3$): δ 0.85 (3H, t, J=6.7 Hz), 1.26 (10H, m), 1.67 (2H, quin J=6.7 Hz), 4.16 (2H, t, J=6.7 Hz), 6.23, 7.54 (each 1H, d, J=15.9 Hz), 6.84 (1H, d, J=8.2 Hz), 6.96 (1H, dd, J=8.2, 2.0 Hz), 7.06 (1H, d, J=2.0 Hz), 8.26 (2H, br s, —OH).

Compound 10

Mp: 87-88 ☐

IRν$_{max}$ (cm$^{-1}$): 3476, 3322, 1677, 1629, 1597, 1527, 1274, 1180, 972, 859, 812

MS m/z (%): 306 (M$^+$, 65), 180 (100), 163 (38), 145 (7), 136 (13), 134 (10), 89 (8)

$^1$H-NMR (CDCl$_3$): δ 0.86 (3H, t, J=6.7 Hz), 1.27 (12H, m), 1.66 (2H, quin J=6.7 Hz), 4.13 (2H, t, J=6.7 Hz), 6.27, 7.52 (each 1H, d, J=16.0 Hz), 6.85 (1H, d, J=8.1 Hz), 7.03 (1H, dd, J=8.1, 2.0 Hz), 7.14 (1H, d, J=2.0 Hz).

Compound 11

Mp: 108-109☐

IRν$_{max}$ (cm$^{-1}$): 3484, 3326, 1678, 1629, 1597, 1527, 1275, 1181, 972, 859, 812

MS m/z (%): 320 (M$^+$, 48), 180 (100), 163 (62), 145 (9), 136 (28), 134 (15), 89 (22)

$^1$H-NMR (CDCl$_3$): δ 0.85 (3H, t, J=6.7 Hz), 1.24 (14H, m), 1.66 (2H, quin, J=6.7 Hz), 4.16 (2H, t, J=6.7 Hz), 5.89, 6.01 (each 1H, br s, —OH), 6.24, 7.55 (each 1H, d, J=16.0 Hz), 6.85 (1H, d, J=8.2 Hz), 6.98 (1H, dd, J=8.2, 2.0 Hz), 7.03 (1H, d, J=2.0 Hz).

Compound 12

Mp: 100-101 ☐

IRν$_{max}$ (cm$^{-1}$): 3482, 3326, 1676, 1630, 1596, 1527, 1274, 1180, 972, 849, 810

MS m/z (%): 334 (M$^+$, 82), 180 (100), 163 (40), 145 (5), 136 (15), 134 (12)

$^1$H-NMR (CDCl$_3$): δ 0.85 (3H, t, J=6.6 Hz), 1.24 (16H, m), 167 (2H, quin, J=6.6 Hz), 4.17 (2H, t, J=6.6 Hz), 6.24, 7.56 (each 1H, d, J=15.9 Hz), 6.85 (1H, d, J=8.1 Hz), 6.98 (1H, dd, J=8.1, 2.0 Hz), 7.08 (1H, d, J=2.0 Hz).

Compound 13; benzyl dihydrocaffeate

Mp: 150-151 ☐

IRν$_{max}$ (cm$^{-1}$): 3461, 3325, 3031, 1627, 1594, 1527, 1274, 1174, 974, 907, 845

MS m/z (%): 270 (M$^+$, 50), 224 (22), 179 (8), 163 (32), 136 (28), 91 (100), 99 (45)

$^1$H-NMR (CD$_3$COCD$_3$): δ 5.20 (2H, s), 6.33, 7.59 (each 1H, d, J=15.9 Hz), 6.86 (1H, d, J=8.1 Hz), 7.05 (1H, dd, J=8.1, 1.7 Hz), 7.17 (1H, d, J=1.7 Hz), 7.21-7.46 (5H, m).

Compound 14

Mp: 125-126 ☐

IRν$_{max}$ (cm$^{-1}$): 3474, 3326, 1672, 1628, 1593, 1527, 1179, 974, 846, 808

MS m/z (%): 284 (M$^+$, 24), 180 (100), 163 (45), 135 (17), 104 (32), 91 (22), 89 (25)

$^1$H-NMR (CDCl$_3$): δ 2.99, 4.39 (each 2H, t, J=6.8 Hz), 6.20, 7.54 (each 1H, d, J=15.8 Hz), 6.85 (1H, d, J=8.0 Hz), 6.95 (1H, d, J=8.0, 2.0 Hz), 7.06 (1H, d, J=2.0 Hz), 7.13-7.35 (5H, m).

Compound 15

Mp: 102-103 ☐

IRν$_{max}$ (cm$^{-1}$): 3482, 3327, 1671, 1629, 1597, 1179, 973, 809, 696

MS m/z (%): 298 (M$^+$, 18), 180 (100), 163 (19), 135 (8), 118 (30), 117 (30), 91 (24)

$^1$H-NMR (CDCl$_3$): δ 2.01 (2H, quin, J=6.8 Hz), 2.72, 4.20 (each 2H, t, J=6.8 Hz), 6.25, 7.55 (each 1H, d, J=15.9 Hz), 6.85 (1H, d, J=8.2 Hz), 6.98 (1H, d, J=8.2, 1.8 Hz), 7.08 (1H, d, J=1.8 Hz), 7.10-7.30 (5H, s).

Compound 16

Mp: amorphous

IRν$_{max}$ (cm$^{-1}$): 3382, 1706, 1601, 1515, 1.279, 1111, 815

MS m/z (%): 195 (M$^+$−1, 45), 136 (54), 123 (100), 107 (10), 91 (18), 77 (22)

$^1$H-NMR (CD$_3$COCD$_3$): δ 2.51, 2.74 (each 2H, t, J=7.2 Hz), 3.58 (3H, s), 6.53 (1H, dd, J=7.8, 2.1 Hz), 6.69 (1H, d, J=2.1 Hz), 6.71 (1H, d, J=7.8 hz).

Compound 17

Mp: amorphous

IRν$_{max}$ (cm$^{-1}$): 3373, 1705, 1601, 1515, 1281, 1193, 1110, 954, 962, 811

MS m/z (%): 210 (M$^+$, 77), 196 (8), 181 (9), 165 (23), 136 (60), 123 (100), 91 (18)

$^1$H-NMR (CD$_3$COCD$_3$): δ 1.17 (3H, t, J=7.1 Hz), 2.50, 2.74 (each, 2H, t, J=7.8 Hz), 4.05 (2H, q, J=7.1 Hz), 6.53 (1H, dd, J=7.9, 1.8 Hz), 6.70 (1H, d, J=1.8 Hz), 6.71 (1H, d, J=7.1 Hz), 7.69 (2H, br s, —OH).

Compound 18

Mp: amorphous

IRν$_{max}$ (cm$^{-1}$): 3382, 1704, 1601, 1515, 1256, 1110, 1032, 952, 865, 812

MS m/z (%): 224 (M$^+$, 40), 195 (12), 181 (20), 164 (21), 152 (14), 139 (42), 136 (82), 123 (100), 110 (16), 91 (31), 77 (25)

$^1$H-NMR (CD$_3$COCD$_3$): δ 0.87 (3H, t, J=6.8 Hz), 1.58 (2H, sext, J=6.8 Hz), 2.51, 2.74 (each 2H, t, J=7.3 Hz), 3.96 (2H, t, J=6.8 Hz), 6.53 (1H, dd, J=8.2, 1.9 Hz), 6.70 (1H, d, J=1.9 Hz), 6.71 (1H, d, J=8.2 Hz), 7.70 (2H, br s, —OH).

Compound 19

Mp: amorphous

IRν$_{max}$ (cm$^{-1}$): 3382, 1701, 1601, 1515, 1441, 1279, 1192, 1110, 1023, 865, 811

MS m/z (%): 238 (M$^+$, 82), 180 (18), 164 (25), 139 (29), 136 (61), 123 (100), 91 (13)

$^1$H-NMR (CD$_3$COCD$_3$): δ 0.88 (3H, t, J=6.7 Hz), 1.31 (2H, sext, J=6.7 Hz), 1.55 (2H, quin, J=6.7 Hz), 2.51, 2.74

(each 2H, t, J=7.6 Hz), 4.01 (2H, t, J=6.7 Hz), 6.53 (1H, dd, J=8.1, 1.8 Hz), 6.69 (1H, dd, J=1.8 Hz), 6.70 (1H, dd, J=8.1 Hz), 7.65 (2H, br s, —OH).

Compound 20
Mp: 68-70
IR$\nu_{max}$ (cm$^{-1}$): 3390, 1702, 1602, 1515, 1439, 1357, 1281, 1110, 811
MS m/z (%): 252 (M$^+$, 52), 195 (2), 181 (28), 164 (10), 139 (40), 136 (78), 123 (100), 91 (21)
$^1$H-NMR (CDCl$_3$): δ 0.87 (3H, t, J=6.8 Hz), 1.28 (4H, m), 1.57 (2H, quin, J=6.8 Hz), 2.51, 2.74 (each 2H, t, J=7.2 Hz), 4.01 (2H, t, J=6.8 Hz), 6.53 (1H, dd, J=8.0, 2.2 Hz), 6.70 (1H, d, J=2.2 Hz), 6.71 (1H, dd, J=8.0 Hz), 7.66 (2H, br s, —OH).

Compound 21
Mp: 64-66
IR$\nu_{max}$ (cm$^{-1}$): 3386, 1702, 1602, 1515, 1439, 1357, 1281, 1110, 811
MS m/z (%): 266 (M$^+$, 42), 195 (3), 181 (36), 164 (8), 139 (42), 136 (75), 123 (100), 91(17), 42 (42)
$^1$H-NMR (CD$_3$COCD$_3$): δ 0.87 (3H, t, J=6.7 Hz), 1.28 (6H, m), 1.57 (2H, quin, J=6.7 Hz), 2.51, 2.74 (each 2H, t, J=7.3 Hz), 4.01 (2H, t, J=6.7 Hz), 6.53 (1H, dd, J=8.1, 1.6 Hz), 6.69 (1H, d, J=1.6 Hz), 6.70 (1H, dd, J=8.1 Hz), 7.60 (2H, br s, —OH).

Compound 22
Mp: 60-62
IR$\nu_{max}$ (cm$^{-1}$): 3388, 1704, 1598, 1511, 1279, 1110, 810
MS m/z (%): 280 (M$^+$, 27), 182 (37), 139 (32), 136 (55), 123 (100), 91 (13), 77 (11), 57 (41), 55 (31)
$^1$H-NMR (CDCl$_3$): δ 0.85 (3H, t, J=6.7 Hz), 1.24 (8H, br s), 1.55 (2H, quin, J=6.7 Hz), 2.55, 2.79 (each 2H, t, J=7.4 Hz), 4.03 (2H, t, J=6.7 Hz), 6.12, 6.30 (each 1H, br s, —OH), 6.57 (1H, dd, J=8.2, 1.5 Hz), 6.67 (1H, d, J=1.5 Hz), 6.73 (1H, d, J=8.2 Hz).

Compound 23
Mp: 52-54
IR$\nu_{max}$ (cm$^{-1}$): 3395, 1701, 1600, 1512, 1279, 1190, 1026, 864, 811, 784
MS m/z (%): 294 (M$^+$, 31), 182 (43), 136 (53), 123 (100), 91 (11), 55 (22)
$^1$H-NMR (CDCl3) δ 0.85 (3H, t, J=6.8 Hz), 1.24 (10H, br s), 1.55 (2H, quin, J=6.8 Hz), 2.55, 2.80 (each 2H, t, J=7.2 Hz), 4.03 (2H, t, J=6.8 Hz), 6.57 (1H, dd, J=8.0, 1.9 Hz), 6.68 (1H, d, J=1.9 Hz), 6.73 (1H, d, J=8.0 Hz).

Compound 24
Mp: 43-45
IR$\nu_{max}$ (cm$^{-1}$): 3400, 1703, 1601, 1515, 1279, 1192, 1110, 1051, 865, 812, 722
MS m/z (%): 308 (M$^+$, 47), 181 (50), 164 (7), 139 (36), 138 (82), 125 (100), 91 (20), 57 (19), 55 (30), 43 (47)
$^1$H-NMR (CD$_3$COCD$_3$): δ 0.86 (3H, t, J=6.8 Hz), 1.28 (12H, br s), 1.55 (2H, quin, J=6.8 Hz), 2.51, 2.74 (each 2H, t, J=7.4 Hz), 4.01 (2H, t, J=6.8 Hz), 6.53 (1H, dd, J=8.0, 2.0 Hz), 6.69 (1H, d, J=2.0 Hz), 6.71 (1H, dd, J=8.0 Hz).

Compound 25
Mp: 53-55
IR$\nu_{max}$ (cm$^{-1}$): 3410, 1702, 1600, 1512, 1280, 1191, 1110, 1039, 865, 810, 721
MS m/z (%): 322 (M$^+$, 52), 182 (90), 139 (43), 137 (37), 136 (100), 123 (95), 91 (15), 60 (32), 55 (38)
$^1$H-NMR (CDCl$_3$): δ 0.85 (3H, t, J=6.7 Hz), 1.24 (14H, br s), 1.55 (2H, quin, J=6.7 Hz), 2.50, 2.73 (each 2H, t, J=7.2 Hz), 4.03 (2H, t, J=6.7 Hz), 6.56 (1H, dd, J=8.1, 2.0 Hz), 6.68 (1H, d, J=1.9 Hz), 6.73 (1H, d, J=8.1 Hz).

Compound 26
Mp: 54-56
IR$\nu_{max}$ (cm$^{-1}$): 3390, 1721, 1598, 1507, 1274, 1189, 1048, 870, 811, 722
MS m/z (%): 336 (M$^+$, 72), 182 (73), 139 (38), 136 (90), 123 (100), 91 (10), 57 (29), 55 (28)
$^1$H-NMR (CDCl$_3$): δ 0.85 (3H, t, J=6.7 Hz), 1.23 (16H, br s), 1.57 (2H, quin, J=6.7 Hz), 2.55, 2.80 (each 2H, t, J=7.1 Hz), 4.03 (2H, t, J=6.7 Hz), 6.64 (1H, dd, J=8.0, 1.8 Hz), 6.68 (1H, d, J=1.8 Hz), 6.73 (1H, d, J=8.0 Hz).

Compound 27
Mp: amorphous
IR$\nu_{max}$ (cm$^{-1}$): 3387, 1702, 1599, 1512, 1278, 1109, 1025, 813, 748, 697
MS m/z (%): 272 (M$^+$, 31), 181 (63), 139 (100), 123 (40), 91 (72), 90 (78), 77 (32), 65 (34), 55 (15), 51 (23)
$^1$H-NMR (CDCl$_3$): δ 2.61, 2.81 (each 2H, J=7.1 Hz), 5.08 (2H, s), 6.56 (1H, dd, J=8.0, 1.9 Hz), 6.64 (1H, d, J=1.9 Hz), 6.72 (1H, d, J=8.0 Hz), 7.24-7.38 (5H, m).

Compound 28
Mp: amorphous
IR$\nu_{max}$ (cm$^{-1}$): 3403, 1702, 1598, 1511, 1278, 1110, 1050, 813, 748, 699
MS m/z (%): 286 (M$^+$, 22), 182 (34), 136 (30), 123 (83), 105 (100), 104 (27), 91 (36), 90 (37), 77 (41), 65 (31), 51 (22)
$^1$H-NMR (CDCl$_3$): δ 2.54, 2.77 (each 2H, t, J=7.3 Hz), 2.88, 4.25 (each 2H, t, J=7.0 Hz), 6.54 (1H, dd, J=8.2, 1.9 Hz), 6.61 (1H, d, J=1.9 Hz), 6.72 (1H, d, J=8.2 Hz), 7.15-7.38 (5H, m).

Compound 29
Mp: amorphous
IR$\nu_{max}$ (cm$^{-1}$): 3404, 1701, 1598, 1512, 1279, 1190, 1109, 1027, 912, 865, 811, 746
MS m/z (%): 300 (M$^+$, 92), 182 (100), 165 (11), 139 (28), 136 (48), 123 (93), 118 (53), 91 (80), 77 (25), 65 (22), 55 (15)
$^1$H-NMR (CDCl$_3$): δ 1.91 (2H, quin, J=6.7 Hz), 2.58, 2.81 (each 2H, t, J=6.7 Hz), 2.62, 4.07 (each 2H, t, J=6.6 Hz), 6.65 (1H, dd, J=8.0, 1.9 Hz), 6.70 (1H, d, J=1.9 Hz), 6.74 (1H, d, J=8.0 Hz), 7.08-7.31 (5H, m).

Compound 31
Mp: 82-83
IR$\nu_{max}$ (cm$^{-1}$): 3279, 3080, 1648, 1607, 1541, 1353, 1246, 1099, 1037, 977, 930, 807
MS m/z (%): 247 (M$^+$, 82), 190 (53), 175 (100), 145 (61), 135 (41), 117 (30), 89 (50), 63 (16)
$^1$H-NMR (CDCl$_3$): δ 0.89 (3H, t, J=7.1 Hz), 1.32 (2H, sext, J=7.1 Hz), 1.50, (2H, quin, J=7.1 Hz), 3.34 (2H, q, J=7.1 Hz), 5.90 (1H, br s, —NH), 5.94 (2H, s), 6.22, 7.48 (each 1H, d, J=15.5 Hz), 6.73 (1H, d, J=8.0 Hz), 6.91 (1H, dd, J=8.0, 1.6 Hz), 6.94 (1H, d, J=1.6 Hz).

Compound 32
Mp: 95-96
IR$\nu_{max}$ (cm$^{-1}$): 3276, 3070, 1650, 1604, 1543, 1494, 1352, 1325, 1246, 1110, 1037, 928, 850, 808
MS m/z (%): 261 (M$^+$, 81), 261 (81), 190 (46), 175 (100), 145 (50), 135 (38), 117 (27), 89 (48), 63 (13)
$^1$H-NMR (CDCl$_3$): δ 0.74 (3H, t, J=6.8 Hz), 1.17 (4H, m), 1.49 (2H, quin, J=6.8 Hz), 3.24 (2H, q, J=6.8 Hz), 5.80 (2H, s), 6.38, 7.39 (each 1H, d, J=15.5 Hz), 6.57 (1H, d, J=8.0 Hz), 6.79 (1H, dd, J=8.0, 1.4 Hz), 6.85 (1H, d, J=1.4 Hz), 7.23 (1H, t, J=6.8 Hz, —NH).

Compound 33
Mp: 75-76
IR$\nu_{max}$ (cm$^{-1}$): 3281, 3072, 1648, 1605, 1542, 1325, 1246, 1100, 1037, 976, 928
MS m/z (%): 275 (M$^+$, 52), 190 (43), 175 (100), 145 (46), 135 (29), 117 (25), 100 (8), 89 (47), 63 (13)

¹H-NMR (CDCl₃): δ 0.76 (3H, t, J=6.7 Hz), 1.23 (6H, m), 1.49 (2H, quin, J=6.7 Hz), 3.28 (2H, q, J=6.7 Hz), 5.84 (2H, s), 6.36, 7.43 (each 1H, d, J=15.5 Hz), 6.61 (1H, d, J=8.0 Hz), 6.82 (1H, dd, J=8.0, 1.6 Hz), 6.86 (1H, d, J=1.6 Hz), 7.03 (1H, t, J=6.7 Hz, —NH).

Compound 34
Mp: 108-109 □
IRν$_{max}$ (cm⁻¹): 3288, 3069, 1641, 1604, 1530, 1254, 1100, 1041, 966, 929, 854, 815, 724
MS m/z (%): 289 (M⁺, 28), 190 (37), 175 (100), 145 (40), 135 (23), 117 (22), 89 (41), 63 (13), 55 (11)
¹H-NMR (CDCl₃): δ 0.84 (3H, t, J=6.6 Hz), 1.25 (8H, m), 1.51 (2H, quin, J=6.6 Hz), 3.32 (2H, q, J=6.6 Hz), 5.79 (1H, br s, —NH), 5.95 (2H, s), 6.21,
7.50 (each 1H, d, J=15.5 Hz), 6.75 (1H, d, J=7.9 Hz), 6.94 (1H, dd, J=7.9, 1.6 Hz), 6.96 (1H, d, J=1.6 Hz).

Compound 35
Mp: 69-70 □
IRν$_{max}$ (cm⁻¹): 3294, 3072, 1642, 1604, 1541, 1352, 1325, 1244, 1098, 1138, 975, 931, 850, 807
MS m/z (%): 303 (M⁺, 28), 190 (35), 175 (100), 145 (40), 135 (23), 117 (22), 89 (34), 63 (13), 55 (9)
¹H-NMR (CDCl₃): δ 0.80 (3H, t, J=6.4 Hz), 1.25 (10H, m), 1.52 (2H, quin, J=6.4 Hz), 3.30 (2H, q, J=6.4 Hz), 5.88 (2H, s), 6.33, 7.44 (each 1H, d, J=15.6 Hz), 6.65 (1H, d, J=8.0 Hz), 6.85 (1H, dd, J=8.0, 1.6 Hz), 6.88 (1H, d, J=1.6 Hz).

Compound 36
Mp: 124-125 □
IRν$_{max}$ (cm⁻¹): 3408, 3070, 1648, 1604, 1350, 1245, 1035, 698
MS m/z (%): 281 (M⁺, 50), 190 (47), 175 (100), 145 (45), 135 (23), 91 (97)
¹H-NMR (CDCl₃): δ 4.51 (2H, d, J=5.7 Hz), 5.94 (2H, s), 6.24, 7.53 (each 1H, d, J=15.5 Hz), 6.74 (1H, d, J=8.0 Hz), 6.92 (1H, dd, J=8.0, 19 Hz), 6.94 (1H, d, J=1.9 Hz), 7.16-7.37 (5H, m).

Compound 37
Mp: 123-125 □
IRν$_{max}$ (cm⁻¹): 3288, 3071, 1650, 1610, 1604, 1575, 1548, 1500, 1358, 1250, 1039, 970, 930, 813
MS m/z (%): 295 (M⁺, 35), 190 (42), 175 (100), 174 (28), 145 (27), 117 (11), 89 (18), 68 (8)
¹H-NMR (CDCl₃): δ 2.84 (2H, t, J=7.2 Hz), 3.58 (2H, q, J=7.2 Hz), 5.85 (2H, s), 6.32, 7.49 (each 1H, d, J=15.5 Hz), 6.66 (1H, d, J=7.9 Hz), 6.86 (1H, dd, J=7.9, 1.5 Hz), 6.90 (1H, d, J=1.5 Hz), 7.17-7.38 (5H, m).

Compound 38
Mp: 126-127 □
IRν$_{max}$ (cm⁻¹): 3295, 1641, 1613, 1543, 1494, 1352, 1320, 1246, 1036, 966, 857, 813, 751
MS m/z (%): 309 (M⁺, 58), 240 (34), 190 (16), 145 (47), 135 (25), 117 (26), 89 (33), 63 (10).
¹H-NMR (CDCl₃): δ 1.84 (2H, quin, J=7.4 Hz), 2.66 (2H, t, J=7.4 Hz), 3.32 (2H, q, J=7.4 Hz), 6.02 (2H, s), 6.53, 7.44 (each 1H, d, J=15.6 Hz), 6.84 (1H, d, J=7.9 Hz), 7.03 (1H, dd, J=7.9, 1.6 Hz), 7.09 (1H, d, J=1.6 Hz), 7.20-7.40 (5H, m).

Compound 39
Mp: 103-104 □
IRν$_{max}$ (cm⁻¹): 3339, 1641, 1558, 1362, 1278, 1117, 976, 848, 809
MS m/z (%): 235 (M⁺, 60), 178 (41), 163 (100), 145 (20), 135 (22), 117 (20), 89 (32), 55 (36)
¹H-NMR (CD₃COCD₃): δ 0.88 (3H, t, J=7.2 Hz), 1.33 (2H, sext, J=7.2 Hz), 1.49 (2H, quin, J=7.2 Hz), 3.31 (2H, q, J=7.2 Hz), 6.46, 7.43 (each 1H, d, J=15.5 Hz), 6.82 (1H, d, J=8.1 Hz), 6.91 (1H, dd, J=8.1, 1.9 Hz), 7.09 (1H, d, J=1.9 Hz).

Compound 40
Mp: 124-125 □
IRν$_{max}$ (cm⁻¹): 3407, 1642, 1587, 1363, 1277, 1111, 974, 813
MS m/z (%): 249 (M⁺, 64), 178 (33), 163 (100), 162 (43), 145 (20), 135 (33), 117 (20), 89 (29), 86 (20), 77 (13)
¹H-NMR (CD₃COCD₃): δ 0.84 (3H, t, J=7.0 Hz), 1.29 (4H, m), 1.53 (2H, quin, J=7.0 Hz), 3.31 (2H, q, J=7.0 Hz), 6.48, 7.45 (each 1H, d, J=15.6 Hz), 6.83 (1H, d, J=8.2 Hz), 6.92 (1H, dd, J=8.2, 1.8 Hz), 7.10 (1H, d, J=1.8 Hz).

Compound 41
Mp: 106-108 □
IRν$_{max}$ (cm⁻¹): 3219, 1648, 1588, 1362, 1278, 1113, 976, 852, 811, 726
MS m/z (%): 263 (M⁺, 32), 178 (45), 164 (75), 163 (100), 162 (43), 145 (12), 135 (23), 117 (16), 100 (26), 89 (27), 84 (15), 77 (13)
¹H-NMR (CD₃COCD₃): δ 0.83 (3H, t, J=6.8 Hz), 1.26 (6H, m), 1.54 (2H, quin, J=6.8 Hz), 3.30 (2H, q, J=6.8 Hz), 6.57, 7.51 (each 1H, d, J=15.6 Hz), 6.84 (1H, d, J=8.1 Hz), 6.92 (1H, dd, J=8.1, 1.6 Hz), 7.12 (1H, d, J=1.6 Hz).

Compound 42
Mp: 126-127 □
IRν$_{max}$ (cm⁻¹): 3347, 1642, 1588, 1545, 1510, 1363, 1266, 1112, 975, 809
MS m/z (%): 277 (M⁺, 42), 192 (10), 178 (32), 163 (100), 145 (12), 135 (20), 114 (14), 98 (8)
¹H-NMR (CD₃COCD₃): δ 0.82 (3H, t, J=6.6 Hz), 1.20 (8H, m), 1.52 (2H, quin, J=6.6 Hz), 3.32 (2H, q, J=6.6 Hz), 6.51, 7.48 (each 1H, d, J=15.6 Hz),
6.83 (1H, d, J=8.1 Hz), 6.92 (1H, dd, J=8.1, 1.5 Hz), 7.11 (1H, d, J=1.5 Hz).

Compound 43
Mp: 111-112 □
IRν$_{max}$ (cm⁻¹): 3286, 1642, 1588, 1520, 1363, 1277, 1112, 975, 811
MS m/z (%): 291 (M⁺, 18), 220 (8), 193 (11), 178 (31), 163 (100), 145 (8), 135 (13), 128 (22), 117 (11), 98 (8), 89 (19), 84 (12)
¹H-NMR (CD₃COCD₃): δ 0.84 (3H, t, J=6.6 Hz), 1.24 (10H, m), 1.52 (2H, quin, J=6.6 Hz), 3.30 (2H, q, J=6.6 Hz), 6.47, 7.42 (each 1H, d, J=15.6 Hz), 6.82 (1H, d, J=8.2 Hz), 6.90 (1H, dd, J=8.2, 1.8 Hz), 7.09 (1H, d, J=1.8 Hz).

Compound 44
Mp: 165-167 □
IRν$_{max}$ (cm⁻¹): 3263, 1641, 1591, 1518, 1354, 1279, 1113, 1080, 1029, 975, 850, 813, 738
MS m/z (%): 269 (M⁺, 18), 164 (27), 163 (1001), 136 (12), 106 (100), 91 (28), 89 (15)
¹H-NMR (CD₃COCD₃): δ 4.50 (2H, d, J=5.8 Hz), 6.56, 7.50 (each 1H, d, J=15.6 Hz), 6.83 (1H, d, J=8.0 Hz), 6.91 (1H, dd, J=8.0 Hz, 1.6 Hz),
7.11 (1H, d, J=1.6 Hz), 7.21-7.36 (5H, m).

Compound 45
Mp: 147-149 μl
IRν$_{max}$ (cm⁻¹): 3288, 1642, 1591, 1523, 1361, 1279, 1036, 975, 849, 812, 749, 700
MS m/z (%): 283 (M⁺, 17), 178 (22), 163 (100), 145 (9), 135 (7), 117 (8), 91 (13)
¹H-NMR (CD₃COCD₃): δ 2.84 (2H, t, J=6.8 Hz), 3.53 (2H, q, J=6.8 Hz), 6.43, 7.43 (each 1H, d, J=15.2 Hz), 6.83 (1H, d, J=8.1 Hz), 6.92 (1H, dd, J=8.1, 1.8 Hz), 7.07 (1H, d, J=1.8 Hz), 7.15-7.30 (5H, m)

Compound 46
Mp: 125-127 □
IRν$_{max}$ (cm⁻¹): 3326, 1642, 1587, 1362, 1279, 1112, 976, 851, 813, 748

MS m/z (%): 297 (M+, 46), 192 (38), 175 (30), 164 (100), 163 (84), 145 (18), 135 (26), 117 (35), 91 (50), 84 (48), 69 (30)

$^1$H-NMR (CD$_3$COCD$_3$): δ 1.86 (2H, quin, J=7.4 Hz), 2.63 (2H, t, J=7.4 Hz), 3.39 (2H, m), 6.59, 7.56 (each 1H, d, J=15.6 Hz), 6.89 (1H, d, J=8.1 Hz), 6.94 (1H, dd, J=8.1, 1.6 Hz), 7.08-7.28 (5H, m).

Compound 47

Mp: 81-82☐

IRν$_{max}$ (cm$^{-1}$): 3291, 3045, 1640, 1530, 1361, 1279, 1111, 810, 783

MS m/z (%): 237 (M+, 79), 165(12), 136(79), 123(100), 115(27), 91(23), 74 (82)

$^1$H-NMR (CDCl$_3$): δ 0.84 (3H, t, J=7.1 Hz), 1.26 (2H, sex, J=7.1 Hz), 1.40 (2H, quin, J=7.1 Hz), 2.42, 2.75 (each 2H, t, J=7.3 Hz), 3.15 (2H, q, J=7.1 Hz), 6.50 (1H, br d, J=7.9 Hz), 6.71 (2H, m), 7.42 (2H, br s. —NH).

Compound 48

Mp: 99-101☐

IRν$_{max}$ (cm$^{-1}$): 3319, 3054, 1630, 1535, 1361, 1279, 1147, 1111, 810

MS m/z (%): 251 (M+, 69), 165(12), 136(64), 123(100), 114(15), 88 (47)

$^1$H-NMR (CD$_3$COCD$_3$): δ 0.85 (3H, t, J=6.8 Hz), 1.22 (4H, m), 1.42 (2H, quin, J=6.8 Hz), 2.36, 2.74 (each 2H, t, J=7.2 Hz), 3.14 (2H, q, J=6.8 Hz), 6.50 (1H, dd, J=8.2, 1.9 Hz), 6.68 (1H, d, J=1.9 Hz), 6.69 (1H, d, J=8.2 Hz), 7.10 (1H, brs. —NH).

Compound 49

Mp: 83-85☐

IRν$_{max}$ (cm$^{-1}$): 3289, 3051, 1630, 1545, 1361, 1278, 1194, 1111, 810

MS m/z (%): 265 (M+, 78), 165(16), 136(63), 123(100), 102(47), 91 (18)

$^1$H-NMR (CD$_3$COCD$_3$): δ 0.84 (3H, t. J=7.0 Hz), 1.24 (6H, brs), 1.41 (2H, quin, J=7.0 Hz), 2.41, 2.75 (each 2H, t, J=7.3 Hz), 3.14 (2H, q, J=7.0 Hz), 6.51 (1H, dd, J=8.0, 2.0 Hz), 6.70 (1H, d, J=8.0 Hz), 6.71 (1H, d, J=2.0 Hz), 7.40 (1H, brs, —NH).

Compound 50

Mp: 114-116☐

IRν$_{max}$ (cm$^{-1}$): 3307, 3044, 1644, 1530, 1279, 1192, 1110, 810

MS m/z (%): 279 (M+, 100), 165(15), 136(72), 123(100), 116(48), 91 (15)

$^1$H-NMR (CD$_3$COCD$_3$): δ 0.85 (3H, t, J=6.7 Hz), 1.25 (8H, br s), 1.42 (2H, quin, J=6.4 Hz), 2.36, 2.74 (each 2H, t, J=7.5 Hz), 3.14 (2H, q, J=6.4 Hz), 6.49 (1H, dd, J=7.9, 1.9 Hz), 6.69 (1H, d, J=1.9 Hz), 6.69 (1H, d, J=7.9 Hz), 7.10 (1H, br s, —NH), 7.80 (2H, brs, —OH).

Compound 51

Mp: 80-82☐

IRν$_{max}$ (cm$^{-1}$): 3286, 3041, 1635, 1540, 1361, 1279, 1110, 809

MS m/z (%): 293 (M+, 100), 165(9), 136(40), 130(25), 123 (35)

$^1$H-NMR (CD$_3$COCD$_3$): δ:0.85 (3H, t, J=6.9 Hz), 1.25 (10H, br s), 1.42 (2H, quin, J=6.9 Hz), 6.50 (1H, dd, J=8.1, 1.9 Hz), 6.69 (1H, d, J=8.1 Hz), 6.70 (1H, d, J=1.9 Hz), 7.18 (1H, br s, —NH), 7.85, 7.97 (each 1H, br s, —OH).

Compound 52

Mp: 149-151☐

IRν$_{max}$ (cm$^{-1}$): 3307, 3050, 1633, 1517, 1279, 1111, 813, 699

MS m/z (%): 271 (M+, 83), 148(51), 136(23), 123(31), 106(31), 91 (100)

$^1$H-NMR (CDCl$_3$): δ 2.50, 2.80 (each 2H, t, J=7.4 Hz), 4.37 (2H, d, J=6.0 Hz), 6.53 (1H, dd, J=8.0, 1.9 Hz), 6.72 (1H, d, J=8.0 Hz), 6.73 (1H, d, J=1.9 Hz), 7.22 (5H, m), 7.67 (1H, br s, —NH), 7.80 (2H, br s, —OH).

Compound 53

Mp: 129-131☐

IRν$_{max}$ (cm$^{-1}$): 3287, 3042, 1633, 1523, 1355, 1195, 1111, 812

MS m/z (%): 285 (M+, 8), 165(21), 136(27), 123(100), 91 (30)

$^1$H-NMR (CDCl$_3$): δ 2.41, 2.73 (each 2H, t, J=6.9 Hz), 2.76 (2H, t, J=6.9 Hz), 3.40 (2H, q, J=6.9 Hz), 6.52 (1H, dd, J=8.0, 1.8 Hz), 6.74 (1H, d, J=1.8 Hz), 6.74 (1H, d, J=8.0 Hz), 7.20 (5H, m), 7.36 (1H, br s, —NH), 8.03 (2H, br s, —OH).

Compound 54

Mp: 127-1291☐

IRν$_{max}$ (cm$^{-1}$): 3351, 3035, 1633, 1523, 1280, 1111, 750, 700

MS m/z (%): 299 (M+, 77), 195(40), 136(81), 123(100), 118(30), 91(73), 77(24), 73 (42)

$^1$H-NMR (CD$_3$COCD$_3$): δ 1.78 (2H, quin, J=7.6 Hz), 2.41, 2.76 (each 2H, t, J=7.4 Hz), 2.57 (2H, t, J=7.6 Hz), 3.19 (2H, q, J=7.6 Hz), 6.52 (1H, dd, J=8.0, 1.9 Hz), 6.71 (1H, d, J=8.0 Hz), 6.72 (1H, d, J=1.9 Hz), 7.20 (5H, m), 7.28 (1H, br s, —NH), 7.90 (2H, br s, —OH).

Compound 55

Mp: 51-52☐

IRν$_{max}$ (cm$^{-1}$): 3030, 1703, 1620, 1595, 1490, 1303, 1264, 1104, 1006, 863

MS m/z (%): 206 (M+, 100), 175(56), 145(21), 117 (9)

$^1$H-NMR (CDCl$_3$): δ 3.77 (3H, s), 5.98 (2H, s), 6.24, 7.58 (each 1H, d, =15.9 Hz), 6.80 (1H, d, J=8.0 Hz), 6.97 (1H, dd, J=8.0, 2.0 Hz), 7.00 (1H, d, J=2.0 Hz).

Compound 56

Mp: liquid $^1$H-NMR (CDCl$_3$): δ 2.54, 2.82 (each 2H, t, J=7.3 Hz), 3.62 (3H, s), 5.87 (2H, s), 6.63 (1H, dd, J=7.9, 1.6 Hz), 6.65 (1H, d, J=1.6 Hz), 6.69 (1H, d, J=7.9 Hz).

Compound 57

Mp: liquid $^1$H-NMR (CDCl$_3$): δ 1.79 (2H, m), 2.57 (2H, t, J=7.7 Hz), 3.60 (each 2H, t, J=6.5 Hz), 4.35 (1H, br s, —OH), 5.86 (2H, s), 6.59 (1H, dd, J=7.9, 1.5 Hz), 6.65 (1H, d, J=1.5 Hz), 6.69 (1H, d, J=7.9 Hz).

Compound 58

Mp: liquid

IRν$_{max}$ (cm$^{-1}$): 3043, 1602, 1500, 1482, 1242, 1114, 1038, 929, 808

MS m/z (%): 194 (M+, 65), 162(44), 136(92), 135(100), 104(27), 77 (37)

$^1$H-NMR (CDCl$_3$): δ 1.81 (2H, m), 2.58 (2H, t, J=7.6 Hz), 3.31 (3H, s), 3.50 (2H, t, J=6.4 Hz), 5.89 (2H, s), 6.61 (1H, dd, J=7.8, 1.4 Hz), 6.67 (1H, d, J=1.5 Hz), 6.71 (1H, d, J=7.8 Hz).

Compound 59

Mp: liquid

IRν$_{max}$ (cm$^{-1}$): 3038, 1602, 1501, 1482, 1242, 1107, 1038, 808

MS m/z (%): 208 (M+, 53), 162(100), 136(82), 135(95), 104(44), 77 (42)

$^1$H-NMR (CDCl$_3$) δ 1.19 (3H, t, J=7.5 Hz), 1.83 (2H, m), 2.59 (2H, t, =7.6 Hz), 3.38 (2H, q, J=7.5 Hz), 3.49 (2H, d, J=7.1 Hz), 5.88 (2H, s), 6.60 (1H, dd, J=7.8, 1.6 Hz), 6.67 (1H, d, J=1.6 Hz), 6.70 (1H, d, J=7.8 Hz).

Compound 60

Mp: liquid

IRν$_{max}$ (cm$^{-1}$): 3051, 1602, 1500, 1481, 1242, 1185, 1113, 1038, 938

MS m/z (%): 222 (M⁺, 37), 162(100), 136(71), 135(71), 104(31), 77 (38)

¹H-NMR (CDCl₃): δ 0.92 (3H, t, J=7.3 Hz), 1.59 (2H, sex, J=7.3 Hz), 1.83 (2H, m), 2.60 (2H, d, J=7.6 Hz), 3.34 (2H, t, J=7.3 Hz), 3.38 (2H, t, J=6.6 Hz), 5.87 (2H, s), 6.61 (1H, dd, J=7.8, 1.5 Hz), 6.67 (1H, d, J=1.5 Hz), 6.70 (1H, d, J=7.8 Hz).

Compound 61
Mp: liquid
IRν$_{max}$ (cm⁻¹): 3050, 1602, 1500, 1482, 1242, 1110, 930, 808
MS m/z (%): 236 (M⁺, 27), 162(100), 136(60), 135(48), 104(27), 77 (31)

¹H-NMR (CDCl₃): δ 0.90 (3H, t, J=7.1 Hz), 1.36 (2H, m), 1.54 (2H, m), 1.83 (2H, m), 2.59 (2H, t, J=7.6 Hz), 3.37 (2H, t, J=7.1 Hz), 3.38 (2H, t, J=6.8 Hz), 5.89 (2H, s), 6.64 (1H, dd, J=7.9, 1.5 Hz), 6.67 (1H, d, J=1.5 Hz), 6.70 (1H, d, J=7.9 Hz).

Compound 62
Mp: amorphous
IRν$_{max}$ (cm⁻¹): 3353, 3051, 1598, 1512, 1279, 1109, 1016, 814
MS m/z (%): 182 (M⁺, 70), 150(48), 133(22), 124(78), 123(100), 104(21), 77 (33)

¹H-NMR (CD₃COCD₃): δ1.17 (2H, m), 2.45 (2H, t, J=7.6 Hz), 3.20 (3H, s), 3.26 (2H, t, J=6.4 Hz), 6.46 (1H, dd, J=8.0, 2.0 Hz), 6.63 (1H, d, J=2.0 Hz), 6.67 (1H, d, J=8.0 Hz), 7.64, 7.70 (each 1H, br s, —OH).

Compound 63
Mp: amorphous
IRν$_{max}$ (cm⁻¹): 3333, 3051, 1599, 1512, 1279, 1188, 1109
MS m/z (%): 196 (M⁺, 63), 150(100), 133(32), 124(73), 123(71), 104(22), 77 (33)

¹H-NMR (CD₃COCD₃): δ1.12 (3H, t, J=7.9 Hz), 1.75 (2H, m), 2.50 (2H, t, J=7.6 Hz), 3.37 (2H, q, J=7.9 Hz), 3.42 (2H, t, J=7.1 Hz), 6.51 (1H, dd, J=8.1, 2.0 Hz), 6.68 (1H, d, J=2.0 Hz), 6.72 (1H, d, J=8.1 Hz).

Compound 64
Mp: amorphous
IRν$_{max}$ (cm⁻¹): 3351, 3049, 1598, 1512, 1277, 1189, 1112, 950, 789
MS m/z (%): 210 (M⁺, 58), 150(100), 133(27), 124(42), 123(63), 104(19), 77 (14)

¹H-NMR (CD₃COCD₃): δ0.88 (3H, t, J=7.4 Hz), 1.53 (2H, sex, J=7.4 Hz), 1.78 (2H, m), 2.51 (2H, t, J=7.6 Hz), 3.32 (2H, t, J=7.4 Hz), 3.35 (2H, t, J=6.4 Hz), 6.51 (1H, dd, J=7.9, 2.0 Hz), 6.69 (1H, d, J=2.0 Hz), 6.73 (1H, d, J=8.0 Hz).

Compound 65
Mp: amorphous
IRν$_{max}$ (cm⁻¹): 3354, 3051, 1598, 1511, 1277, 1110, 811
MS m/z (%): 224 (M⁺, 37), 150(100), 133(20), 132(27), 124(37), 123(52), 104(12), 77 (15)

¹H-NMR (CDCl₃): δ0.89 (3H, t, J=7.4 Hz), 1.37, 1.50, 1.76 (each 2H, m), 2.50 (2H, t, J=7.4 Hz), 3.34 (2H, t, J=6.6 Hz), 3.36 (2H, t, J=6.4 Hz), 6.50 (1H, dd, J=8.1, 2.1 Hz), 6.68 (1H, d, J=8.1 Hz), 7.68, 7.73 (each 1H, br s, —OH).

Compound 638A
Mp: 125-126☐
¹H-NMR (CD₃COCD₃): δ2.77 (2H, t, J=7.2 Hz), 3.51 (2H, q, J=7.2 Hz), 3.76 (3H, s), 3.78 (3H, s), 6.42, 7.39 (each 1H, d, J=15.6 Hz), 6.74 (1H, dd, J=8.4, 2.0 Hz), 6.81-6.85 (3H, m), 6.91 (1H, dd, J=8.4, 2.0 Hz), 7.05 (1H, d, J=2 Hz).
¹³C NMR: 35.7, 41.4, 55.6, 55.7, 112.2, 113.0, 114.1, 115.6, 118.8, 120.7, 120.9, 127.6, 132.4, 139.9, 145.5, 147.1, 148.0, 149.4, 165.9

Compound 638B
Mp: 198 ☐
¹H NMR (400 MHz, CD₃COCD₃): 2.83 (2H, t, J=6.8 Hz), 3.54 (2H, q, J=6.8 Hz), 6.41, 7.40 (each 1H, d, J=16.0 Hz), 6.82 (1H, d, J=8.0 Hz), 6.92 (1H, dd, J=8.0, 1.8 Hz), 7.06 (1H, d, J=1.8 Hz), 7.20 (21H, d, J=8.0 Hz), 7.44 (2H, d, J=8.0 Hz)
13C NMR: 35.9, 41.4, 114.7, 116.1, 119.2, 120.2, 121.3, 128.0, 131.6, 132.0, 139.8, 140.6, 146.0, 147.7, 166.6

Compound 638C
Mp: 174-177☐
¹H NMR (400 MHz, CD₃COCD₃): 2.72 (2H, t, J=7.2 Hz), 3.45 (2H, q, J=7.2 Hz), 6.40, 7.37 (each 1H, d, J=16.2 Hz), 6.73 (2H, d, J=8.4 Hz), 6.80 (1H, d, J=8.4 Hz), 6.90 (1H, dd, J=8.4, 1.6 Hz), 7.03-7.04 (3H, m).

Compound 638D
¹H NMR (400 MHz, CD₃COCD₃): 3.75 (3H, s), 4.42 (2H, d, J=6.0 Hz), 6.49, 7.44 (each 1H, d, J=16.0 Hz), 6.81-6.94 (4H, m), 7.07 (1H, d, J=1.6 Hz), 7.25 (2H, dd, J=8.8, 2.4 Hz)
¹³C NMR: 43.2, 55.5, 114.4, 114.7, 116.1, 119.3, 121.4, 128.2, 129.6, 132.2, 140.8, 146.0, 147.7, 159.5, 166.4

Compound 638E
¹H NMR (400 MHz, CD₃COCD₃): 4.50 (2H, d, J=6.0 Hz), 6.52, 7.46 (each 1H, d, J=15.6 Hz), 6.83 (1H, d, J=8.0 Hz), 6.93 (1H, dd, J=8.0, 1.8 Hz), 7.08 (1H, d, J=1.8 Hz), 7.19-7.34 (5H, m).

Compound 638F
¹H NMR (400 MHz, CD₃COCD₃): 3.77 (3H, s), 6.59, 7.66 (each 1H, d, J=16.0 Hz), 6.83-6.88 (3H, m), 6.96 (1H, d, J=8.0 Hz), 7.09 (1H, s), 7.66 (2H, d, J=8.8 Hz).

Compound 638G
¹H NMR (400 MHz, CD₃COCD₃): 6.59, 7.53 (each 1H, d, J=15.4 Hz), 6.84 (1H, d, J=8.0 Hz), 6.97 (1H, dd, J=8.0, 2.2 Hz), 7.11 (1H, d, J=2.2 Hz), 7.45 (2H, d, J=8.8 Hz), 7.73 (2H, d, J=8.8 Hz).

Compound 638H
¹H NMR (400 MHz, CD₃COCD₃): 6.56, 7.49 (each 1H, d, J=15.6 Hz), 6.77 (2H, d, J=8.8 Hz), 6.83 (1H, d, J=8.0 Hz), 6.96 (1H, dd, J=8.0, 2.0 Hz), 7.08 (1H, d, J=2.0 Hz), 7.56 (2H, d, J=8.8 Hz).

Compound 638I
Mp: 174-176☐
¹H NMR (400 MHz, CD₃COCD₃): 4.51 (2H, d, J=6.0 Hz), 6.49, 7.44 (each 1H, d, J=16.0 Hz), 6.82 (1H, d, J=8.2 Hz), 6.93 (1H, dd, J=8.2, 2.0 Hz), 6.95-7.00 (1H, m), 7.06 (1H, d, J=2.0 Hz), 7.06-7.16 (2H, m), 7.30-7.36 (1H, m).

Compound 639A
Mp: 126-127☐
¹H NMR (400 MHz, CD₃COCD₃): 2.88 (2H, t, J=7.2 Hz), 3.65 (2H, q, J=7.2 Hz), 3.87 (3H, s), 3.88 (3H, s), 6.17, 7.53 (each 1H, d, J=15.6 Hz), 6.82 (1H, d, J=8.4), 6.98 (1H, d, J=2.0 Hz), 7.04 (1H, dd, J=8.4, 2.0 Hz), 7.20-7.33 (5H, m)
¹³C NMR: 36.6, 41.7, 56.0, 56.1, 110.9, 112.4, 120.4, 122.2, 126.8, 128.9, 129.1, 129.3, 129.4, 140.0, 150.2, 151.5, 166.2.

Compound 639B
¹H NMR (400 MHz, CD₃COCD₃): 2.27 (3H, s), 2.28 (3H, s), 2.86 (2H, t, J=7.2 Hz), 3.54 (2H, q, J=7.2 Hz), 6.37, 7.49 (each 1H, d, J=15.6 Hz), 7.25 (1H, d, J=8.0 Hz), 7.44 (1H, dd, J=8.0, 2.0 Hz), 7.47 (1H, d, J=2.0 Hz), 7.16-7.32 (5H, m).

Compound 639C
¹H NMR (400 MHz, CD₃COCD₃): 2.26 (3H, s), 2.85 (2H, t, J=7.2 Hz), 3.54 (2H, q, J=7.2 Hz), 6.49, 7.44 (each 1H, d, J=15.6 Hz), 6.96 (1H, d, J=8.0), 7.04 (1H, s), 7.18 (1H, d, J=8.0 Hz), 7.22-7.32 (5H, m).

¹H NMR (400 MHz, CD₃COCD₃): 2.25 (3H, s), 2.85 (2H, t, J=7.2 Hz), 3.54 (2H, q, J=7.2 Hz), 6.56, 7.45 (each 1H, d, J=15.6 Hz), 6.96 (1H, d, J=8.0), 7.05 (1H, s), 7.18 (1H, d, J=8.0 Hz), 7.22-7.32 (5H, m).

Compound 640
¹H NMR (400 MHz, CD₃COCD₃): 2.86 (2H, t, J=7.4 Hz), 3.55 (2H, q, J=7.4 Hz), 3.83 (3H, s), 6.54, 7.49 (each 1H, d, J=15.6 Hz), 6.84 (1H, d, J=8.4), 7.04 (1H, dd, J=8.4, 1.8 Hz), 7.14 (1H, d, J=1.8 Hz), 7.15-7.25 (5H, m).

Compound 642A $^1$H NMR (400 MHz, CD$_3$COCD$_3$): 3.01 (3H, s), 4.67 (2H, s) 6.97, 7.57 (each 1H, d, J=15.2 Hz), 6.76-6.85 (2H, m), 7.16 (1H, s), 7.26-7.35 (5H, m).

Compound 642B

Mp: amorphous $^1$H NMR (400 MHz, CD$_3$COCD$_3$): 2.87 (2H, t, J=7.2 Hz), 3.01 (3H, s), 3.53 (2H, t, J=7.2 Hz), 6.68, 7.49 (each 1H, d, J=15.2 Hz), 6.77-6.91 (2H, m), 7.07 (1H, s), 7.22-7.38 (5H, m).

Compound 642C $^1$H NMR (400 MHz, CD$_3$COCD$_3$): 1.79-1.89 (4H, m), 3.44 (2H, t, J=6.8 Hz), 3.66 (2H, t, J=6.8 Hz), 6.70, 7.42 (each 1H, d, J=15.4 Hz), 6.82 (1H, d, J=8.0 Hz), 6.99 (1H, d, J=8.0 Hz), 7.13 (1H, s).

Compound 642D $^1$H NMR (400 MHz, CD$_3$COCD$_3$): 1.54-1.64 (6H, m), 3.53-3.61 (4H, m), 3.66 (2H, t, J=6.8 Hz), 6.82 (1H, d, J=8.2 Hz), 6.96, 7.43 (each 1H, d, J=15.2 Hz), 7.01 (1H, dd, J=8.2, 1.6 Hz), 7.14 (1H, d, J=1.6 Hz).

The pharmaceutical composition of the present invention could be in the form of a liquid or a patch directly pasting on local wound area with all kinds of excipients, carriers, and diluents if necessary. The formulation can be in the form of pastilles, tablets, and capsules with adding a binder, such as starch or sodium carboxymethyl cellulose according the conventional methods. The formulation also can be in the form of the sustained-release pastilles or capsules by adding the sustained-release reagents. However, the present invention provides a manufacturing process of the present formulation to produce double pastilles or mixture particles with different release level based on the desired particle size, or alternatively to produce an formulation by encapsulating the particle having various size with immediate release film-coated pastilles, slow release film-coated pastilles, and anti-acidity film-coated pastilles.

The first aspect of the present invention is to provide a compound for preventing or treating the diabetics and the implications thereof, wherein the compound is the catechol-based derivatives. The present invention further provides a pharmaceutical composition which comprises a therapeutically effective amount of the compound and the pharmaceutical acceptable carriers or the excipients.

Pharmacological Activity

The pharmacological data of the compounds of the present invention is evaluated in vivo.

I. Capacities of the Compound to Reduce the Blood Sugar (a) Male Wistar rats are provided from the National Laboratory Animal Breeding and Research Center (Taipei, Taiwan), each of whose weight is about 200-250 grams, and the average age thereof is above 8 weeks. They were housed under conditions of constant temperature (25±1□) and controlled illumination (light time and dark time are respectively 12 hours). Food and water were available.

(b) Streptozocin-induced type 1 diabetic rats: the male Wistar rats of 8 weeks age undergo a starvation for 72 hours, followed by anaesthetizing the rats by injecting with 30 mg/kg pentobarbital into the abdominal cavity. After the rats fall asleep, 60 mg/kg streptozotocin (STZ) is administrated by an intravenous injection. After a week, phlebotomize and obtain a value of blood sugar by a glucose kit, wherein the glucose kit is further analyzed by Biosystem S.A., Barcelona Spain, BST330. While the value of the blood sugar is greater than 400 mg/dL and the typical three symptoms, eating more, drink more, micturition occur, it is deemed as Type 1 Diabetic rats.

(c) Insulin-induced type 2 diabetic rats: the abdominal cavity of the male Wistar rats of 12 weeks age are injected with 0.5 IU/kg long-term insulin (MonotardR HM) three times a day for fourteen days. Then, the 10 mg/kg tolbutamide, an anti-diabetic drug of sulfonylurea class, is injected into the abdominal cavity. Phlebotomize 0.1 ml blood respectively at the preadministration and the postadministration of sixty minutes, and calculate the reduced value of the blood sugar. If the variation of the ability of lowering blood sugar is less than 10%, which is deemed as the type II (insulin resistance) diabetes rat.

(d) The administration: Dissolve the medicine equivalently in deionized water, and then administrate the mentioned solution into the normal and diabetic rats by an orally perfusion. Keep with the desired concentration of the perfusion amount by taking suitable amount of the medicine solution according to the weight of the different animal.

(e) Detection of the Blood Sugar

The rats to be experimented should undergo a starvation for 8-12 hours overnight. Next day, the rats are anesthetized with 30 mg/kg pentobarbital by injecting into the abdominal cavity. After the rats fall asleep, fix the rats on the board with the rubber band. Open the groin, find the veins, bleed 0.1 ml blood from an empty stomach, and then feed the medicine into the body of the rats by taking orally. After 90 minutes, bleed and perform a centrifugation (13,000 rpm, 5 minutes) to separate the serum and the plasma. Take the 10 μl supernatant of the serum and add 1 ml reagent of the glucose kit thereinto by gently mixing. React for 5 minutes at 37□, followed by detecting the value of the blood sugar by means of BST330 based on the different absorption level. The principal of the glucose kit depends on the level of the glucose being oxidized into glucuronic acid and hydrogen peroxide, which exhibits different levels of red color. The value of the blood sugar (mg/dL) is calculated by comparing the level of redness with contrasting the standard curve.

(f) Calculation for Percentage of Lowering Blood Sugar (The value of blood sugar at postadministration)−(The value of blood sugar at preadministration)/(The value of blood sugar at preadministration)×100%

(g) Statistical Method

The results of the experiments are presented in the average value±the standard error (mean±SE), and the variations therebetween are evaluated according to the Student's t-test, while the variations thereamong are evaluated according to one-way ANOVA and Bonferroni's t-test, wherein P<0.05 is deemed to have apparent differences.

II. The Evaluations of the Compound on Flow Rate of the Coronary Artery (h) The Evaluations on the Flow Rate of the Coronary Artery Each of the male Wistar rats weighs about 200-250 grams, and is anesthetized with 25 mg/kg pentobarbital and 16 mg/kg heparin by injecting into the abdominal cavity. After falling asleep, separate the cervical vertebra and immediately take the heart out hanging on the constant pouring pressure circulation instrument (Langendorff, AD Instruments Pty Ltd, ML870B2) and fill a 37□ pouring solution of 95% of oxygen and 5% of carbon dioxide with the artery (119.7 mM NaCl, 23.8 mM NaHCO$_3$, 5.6 mM glucose, 1.2 mM CaCl$_2$, 1.1 mM MgCl$_2$, 0.3 mM NaH$_2$PO$_4$, and 5.0 mM KCl), which washes the heart and clean out the blood water by pouring in a reverse direction. The rate of the reverse pouring is 10 ml/min, followed by maintaining the pouring pressure of the coronary artery at 80 mmHg. After balancing for thirty minutes, measure the rate of the pouring solution flowing in the heart, and observe the change of the rate the pouring solution flowing in the heart while the testing drug is added.

(i) The coronary artery ligature of the living rat—the heart protective evaluations at the reperfusion model.

The grown-up male rats having the weight of 250~300 grams (Sprague-Dawley strain, purchased BioLASCO Taiwan Co., Ltd.) are anesthetized with 1.25 g/kg urethane by the abdominal cavity injection. After anaesthetization, cut the trachea, connect with the artificial respirator (Harvard Rodent Ventilator Model 983), give 15 ml/kg of the tidal volume, and control the respiratory rate at 668 strokes/min, followed by cutting off both sides of the vagus immediately. After the intubation of the right arterial carotis, it is connected to the pressure converter (Statham P23XL transducer) so as to monitor the changes of systemic blood pressure. In addition, the rats' four limbs are connected to the silver electrode, so as to record the changes of the electrocardiogram (ECG). Blood pressures, heartbeats and electrocardiogram curves are recorded and analyzed by the software (MacLab data acquisition system, AD Instrument Pty, Castle Hill, NSW, Australia).

After all previous preparations have been done, open the ribcage by the thoracotomy and cut off the skin layers and muscles to find the rib. Burn the fourth and fifth rib close to 2 mm of the sternum in an electrical knife and stabilize the injury with the retractor followed by rending the pericardial membrane, separating the left atrial appendage gently by the cottons, and clasping the anterior interventricular branch of the left coronary artery immediately between the left atrial appendage and the pulmonary artery by a needle forceps having a silk yarn with a hook. Put loops on both ends of silk yarn to seal the wound by unclamping the retractor. Balance in 15 minutes, and if there exists cardiac arrhythmia or the systolic pressure is lower than 80 mmHg, it will be eliminated.

After the balance, the acute cardiac muscle ischaemia is caused by pushing the loop passed by a silk yarn with a hemostat downwards to be stabilized. Then, unclamp the hemostat and uplift the loop to perform a reperfusion of the coronary artery being ligated by the silk yarn. While the flow of the coronary artery is successively blocked, the ischaemic area should appear the cyanosis, where some indicators of the cardiac ischaemia could be observed, including the lowering pressure of the coronary artery and the changed electrocardiography (R wave broadens, and ST section raises), which is achieved by means of the same strength of pushing downwards during each surgery. If the same surgical procedure is performed, the rat without administrating the drug and performing an ischaemia and an ischaemia/reperfusion is regarded as the sham group. The rundown of the ischaemia and the ischaemia/reperfusion of the present test is as follows.

Perform an ischaemia for 45 minutes and perform an ischaemia/reperfusion for 2 hours. Administrate by injecting the drug into the abdominal cavity after perform the ischaemia for 15 minutes.

(i-1) Detection of the Heart Intract Size

If the rat does not die from the cardiac arrhythmia, push the loop downwards again to block the blood flow after the reperfusion is finished. Inject the approximately 2 ml, 1% methylene blue into the ischaemic area via a jugular vein, where the non-ischemic area is dyed as purple and the ischemic area or area at risk is retained as red. Subsequently, the heart is immediately took out and washed by the physiological salt solution to remove the connective tissue of the atrium and the surplus water. Cut the undyed ischemic area and weight the total ventricle to calculate the ischemic area of the ventricle.

Area at risk (% of total ventricular)=(Weight of risk area)/(Total ventricular weight)×100%.

Cut the ischemic area into a slice with the thickness of approximately 1 mm. Immerse the slice into a TTC (2,3,5-triphenyltetrazolium chloride, in saline) solution, and heat the resultant solution at the 37□ incubator for 30 minutes, followed by replacing the solvent with 10% formaldehyde solution to preserve the resulting solution for two weeks. The living cells are able to produce the dehydrogenase, which could reduce TTC to a crimson formazan precipitate, whereas the dead cells are unable to produce dehydrogenase, which decolor the formazan as a gray precipitate. Cut and weight the gray infraction area and calculate the ratio.

Infract Size (% of risk area)=(Weight of infraction)/ (Weight of risk area)×100%.

Please refer to Table 10, which shows the result of the changes of blood sugar in the treatment of the compound 370G among the normal rats and the diabetic rats. This test is performed by orally administrating the compound 370G. It is found that the phenomenon of reducing the blood sugar are shown on the normal rats and the type II diabetics rats when they are orally administrated the compound 370G, a catechol-based derivative, with the dosage ranging from 0.05 to 1.0 mg/kg, wherein *P is smaller than 0.05 and the blank solution is orally administrated as a control contrast.

TABLE 10

| 370G (45) (mg/kg) | Normal rats % decrease in plasma glucose | n | Type 2 diabetic rats % decrease in plasma glucose | n | Type 1 diabetic rats % decrease in plasma glucose | n |
|---|---|---|---|---|---|---|
| Vehicle (control) | 5.8 ± 5.7 | 8 | 2.6 ± 1.2 | 8 | 0.6 ± 0.1 | 8 |
| 0.01 | 11.4 ± 3.1 | 8 | — | — | — | — |
| 0.05 | 32.0 ± 1.1* | 8 | 7.4 ± 2.6 | 5 | — | — |
| 0.1 | 32.9 ± 2.3* | 7 | 17.2 ± 2.6* | 5 | 11.8 ± 5.5* | 5 |
| 0.5 | 32.8 ± 3.4* | 6 | 20.1 ± 3.4* | 6 | 13.8 ± 4.3* | 6 |
| 1.0 | 29.5 ± 1.7* | 6 | 23.3 ± 3.3* | 8 | 11.6 ± 1.7* | 8 |

Please refer to Table 14, which shows the comparative result of the changes of blood sugar in the treatment of the compound 370G at the preadministration and the postadministration. It is found that the compound 370 G has the strongest effect for reducing the blood sugar on the normal rat while having the weakest effect on the type I diabetic rat. Please refer to Table 11, which shows the result of the changes of the insulin's concentration in the treatment of the compound 370G at the preadministration and the postadministration. After orally administrating the compound 370G with the dosage of 1.0 mg/kg, the secretion of insulin can be increased in 60 minutes (*P<0.05), which suggested that the compound 370G for reducing the blood sugar may be associated with enhancement of the secretion of insulin. However, it is also observed that the dominant effect for reducing the blood sugar on the type I diabetic rats, which are incapable of secreting insulin. Therefore, it is suggested that the compound 370G for reducing the blood sugar involves another kind of mechanism associated with the blood sugar reduction in addition to enhance the release of insulin.

TABLE 11

| 370G (45)<br>(1 mg/kg, p.o.) | Pre-treatment | Post-treatment (30 min) |
|---|---|---|
| Insulin (μIU/ml) | 7.7 ± 1.0 | 14.9 ± 3.4* |

TABLE 14

| | Pre-treatment | Post-treatment | | |
|---|---|---|---|---|
| Catechol<br>Derivatives<br>(0.5 mg/kg) | Plasma<br>glucose<br>(mg/dL) | Plasma<br>glucose<br>(mg/dL) | % decrease in<br>plasma glucose | n |
| Vehicle (control) | 138.5 ± 5.9 | 129.3 ± 2.2 | 5.8 ± 5.7 | 8 |
| 639 B | 116.7 ± 2.8 | 84.0 ± 5.0# | 28.1 ± 3.3* | 3 |
| 371G | 108.0 ± 4.2 | 76.7 ± 1.8# | 28.8 ± 3.3* | 3 |
| 370G (45) | 120.5 ± 5.3 | 81.0 ± 5.7# | 32.8 ± 3.4* | 6 |
| 639 C | 104.2 ± 9.9 | 83.4 ± 3.9 | 19.3 ± 4.1 | 5 |
| 370 D | 90.7 ± 3.6 | 74.9 ± 3.6# | 17.5 ± 1.9 | 7 |
| 638 B | 98.1 ± 5.2 | 76.8 ± 4.1# | 21.4 ± 3.0* | 8 |
| 638 A | 102.5 ± 2.4 | 83.6 ± 1.9# | 18.1 ± 2.9 | 8 |
| 615 (37) | 138.3 ± 4.1 | 105.2 ± 3.5# | 23.9 ± 2.1* | 6 |

Please refer to Table VI, which shows the result of the changes of blood sugar respectively in the treatment of the compound 370G and Rosiglitazone. Rosiglitazone is a kind of insulin sensitizer. The compound 370G and Rosiglitazone are orally administrated into the type II diabetic rats for 90 minutes, and then detect the plasma glucose concentration. It is found that the type II diabetic rats having the insulin impedance have the similar effect for reducing the blood sugar with the commercial insulin sensitizer.

TABLE VI

| Treatment | % decrease in plasma glucose | n |
|---|---|---|
| Rosiglitazone (1 mg/kg, p.o.) | 15.6 ± 6.3 | 8 |
| 370G (45)<br>(0.5 mg/kg, p.o.) | 20.0 ± 7.7 | 8 |

Please refer to FIG. 1, which shows the result of the changes of the intravenous glucose tolerance test (IGTT) in the treatment of the compound 370G It is found that the glucose availability of the rats is raised in the oral administration of the compound 370G with the dosage of 0.5 mg/ml/kg as compared the results of the control contrast (*P<0.05), which is administrated with 1000 mg/kg glucose for 30 minutes by an intravenous injection.

Please refer to Table 13, which shows the result of the survival rate after orally administrating the compound 370G into the type I diabetic rats. Table 13 is a safety evaluation, wherein the type I diabetic rats are respectively orally administrated with the compound 370G at the dosage of 10 mg/kg and 30 mg/kg. After seven days, it is found that the administration of the compound 370G at the respective dosage of 10 mg/kg and 30 mg/kg do not affect the survival rate of the rats.

TABLE VII

| 370G (45) Treatment | Survival rate (%) of rats | n |
|---|---|---|
| 10 mg/kg, p.o. | 100% | 4 |
| 30 mg/kg, p.o. | 100% | 4 |

In comparison with the ability of other compounds of catechol-based derivatives for reducing the blood sugar, wherein the results shown in Table 14, it is found that these compounds are dominant on reducing the blood sugar after the oral administration of the catechol-based derivatives. The statistics of *P<0.05 means the distinguishable variation as compared with the control contrast, and the statistics of *P<0.05 means the distinguishable variation as compared with the pre-treatment contrast.

The present compounds of the catechol-based derivatives exhibit good effect on reducing the blood sugar for the normal and the diabetic rats at the lower dosages ranging from 0.05 to 1 mg/kg, whereas the survival rate of the rats are not influenced at the higher dosages of respective 10 mg/kg and 30 mg/kg. Therefore, this kind of catechol-based derivatives could be developed to be a potential anti-diabetics drug.

The second aspect of the present invention is to provide a catechol-based derivative for preventing and/or treating ischemics and the complication thereof, and to provide a pharmaceutical composition comprising the above derivative, including the therapeutically effective amount of the catechol-based derivative selected form the group consisting of the formula (I) and a pharmaceutical acceptable carrier or an excipient.

Please refer to Table 15 and 16, which respectively show the result of the coronary flow rate in the treatment of the catechol-based derivatives. It is found that the respective compound 370G, 638J, 640, 638I, 642A, 642B, 639B, and 639C are capable of increasing the coronary flow rate of Wistar rats, which suggests that this kinds of catechol-based derivatives are capable of increasing the coronary flow rate and reducing the injury areas of cardiac muscles resulting from the myocardial ischemia-reperfusion.

TABLE 15

| | coronary flow (ml/min) | | | | | | | |
|---|---|---|---|---|---|---|---|---|
| conc. (μM) | 370G (45) | n | 638H | n | 640 | n | 638I | n |
| 0 | 11.8 ± 1.0 | 5 | 9.0 ± 0.3 | 3 | 9.7 ± 1.3 | 4 | 7.4 ± 0.7 | 3 |
| 0.1 | 12.4 ± 1.1 | 5 | 9.0 ± 0.5 | 3 | 10.1 ± 1.5 | 4 | 7.1 ± 0.5 | 3 |
| 0.3 | 13.2 ± 1.4* | 5 | 8.9 ± 0.5 | 3 | 10.2 ± 1.4 | 4 | 7.1 ± 0.5 | 3 |
| 1 | 15.6 ± 1.2* | 5 | 9.1 ± 0.5 | 3 | 10.3 ± 1.5 | 4 | 7.6 ± 0.8 | 3 |
| 3 | 17.4 ± 1.3* | 5 | 10.1 ± 0.7 | 3 | 11.0 ± 1.5* | 4 | 8.2 ± 0.8 | 3 |
| 10 | 19.5 ± 0.7* | 4 | 13.1 ± 1.0* | 3 | 14.6 ± 2.2* | 4 | 9.3 ± 0.7* | 3 |

TABLE 16

| conc. (μM) | coronary flow (ml/min) | | | | | | | |
|---|---|---|---|---|---|---|---|---|
| | 642A | n | 642B | n | 639B | n | 639C | n |
| 0 | 10.0 ± 0.7 | 3 | 9.8 ± 2.1 | 3 | 7.4 ± 0.2 | 3 | 11.9 ± 2.0 | 3 |
| 0.1 | 12.9 ± 0.4* | 3 | 9.8 ± 2.1 | 3 | | | | |
| 0.3 | 14.2 ± 0.8* | 3 | 10.4 ± 1.7 | 3 | | | | |
| 1 | 16.8 ± 1.6* | 3 | 12.8 ± 1.9 | 3 | 9.0 ± 0.4* | 3 | 13.5 ± 1.5 | 3 |
| 3 | 19.8 ± 2.1* | 3 | 17.4 ± 1.9* | 3 | 11.6 ± 0.6* | 3 | 17.2 ± 1.8* | 3 |
| 10 | | | 23.2 ± 1.7* | 3 | | | | |

Figure 2:
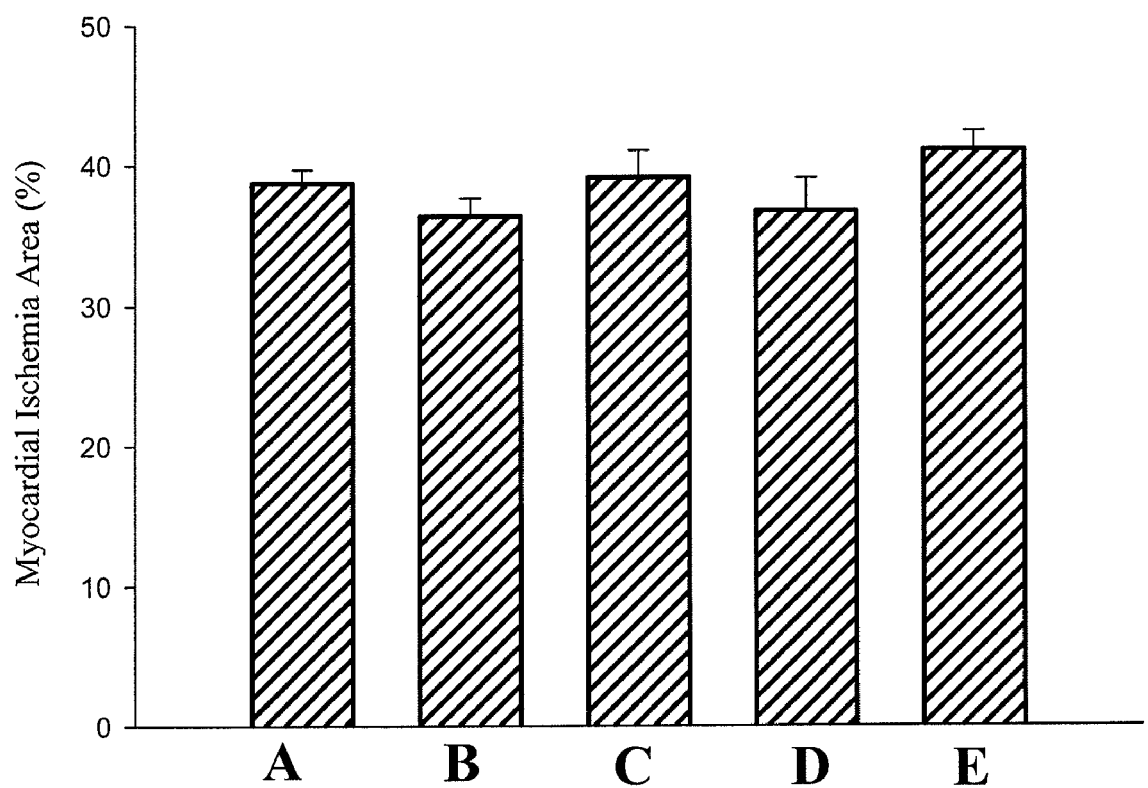
FIG. 2 shows areas at risk of ischemia after the coronary artery is ligated.

Please refer to FIG. 2, which shows the results of the ischemic areas at risk after the coronary artery is ligated. The coronary artery of the rat heart is ischaemic by ligating for 45 minutes, and the blood vessel is unclamped for the reperfusion for two hours, wherein some tissues of the local ischemic area will be deteriorated. After comparing the respective ratio of the areas at risk in the overall area between the control contrast that orally administrated with DMSO and PEG solvents and the trial tests that orally administrated with the compound 370G at the dosages of respective $10^{-6}$ mg/kg, $10^{-5}$ mg/kg, and 15 mg/kg, it is found that the ratio variations thereof are non-obvious. (The ratio in the treatment of DMSO, PEG, and the compound 370G at the dosages of $10^{-6}$ mg/kg, $10^{-5}$ mg/kg, and 15 mg/kg are respectively 38.7±1.0%, of 36.4±1.3%, of 39.1±1.9%, 36.7±2.3%, and 41.1±1.3%).

Figure 3:
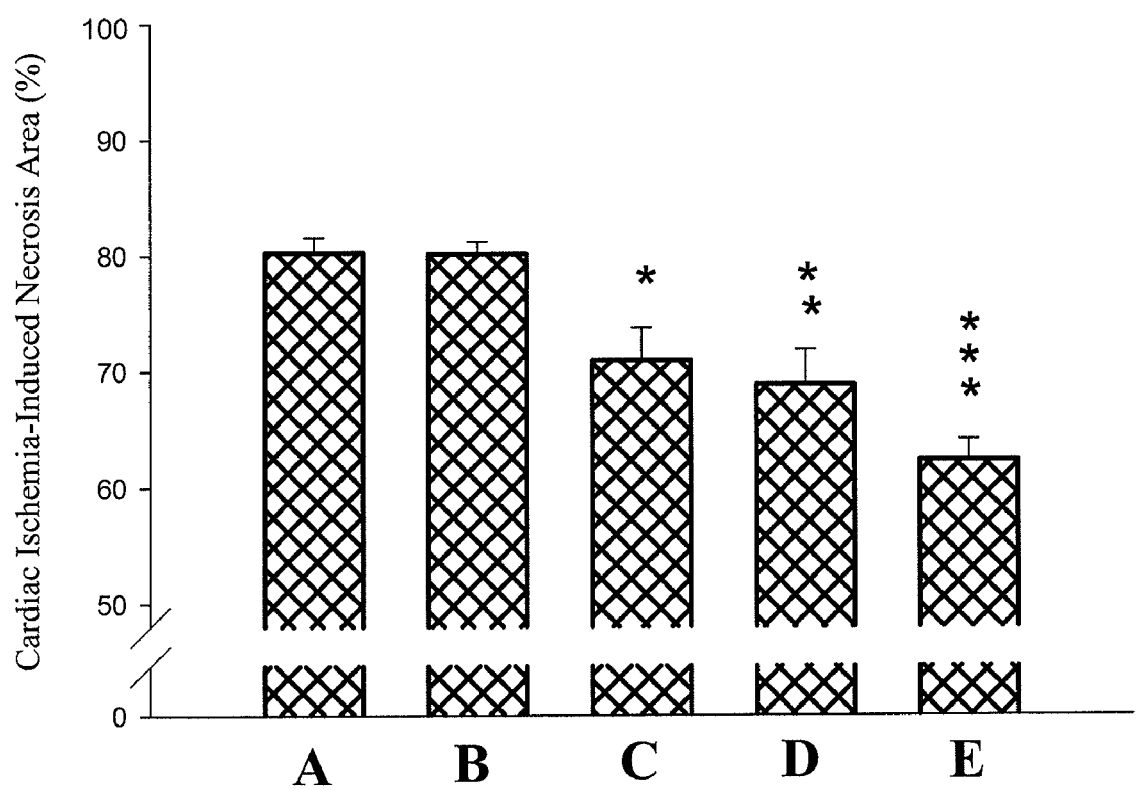
FIG. 3 shows the ratios of the cardiac infract size in response to treatment with 370G at different doses.

Please refer to FIG. 3, which shows the ratios of the cardiac infract size in the treatment of 370G at the different dosages. The ratio of both DMSO and PEG, which serve as the contrast agents, are respectively 80.2±1.2% and 80.1±1.0%. Surprisingly, the infract size is reduced to 70.9±2.8 in the oral administration of the compound 370G at the dosage of $10^{-6}$ mole/kg (approximately 0.28 mg/kg); the infract size is reduced to 68.8±2.9% in the oral administration of the compound 370G at the dosage of $10^{-5}$ mole/kg (approximately 2.8 mg/kg); and the infract size is reduced to 62.8±1.8% in the oral administration of the compound 370G at the dosage of 15 mole/kg. Therefore, the mentioned results show the distinguishable variation as compared with the contrast agents, wherein * represents p<0.05,  represents p<0.01, and * represent p<0.001).

Please refer to Table 15 and 16 again. In the animal tests of the coronary artery ligature and the reperfusion, it is found that in the treatment of the coronary artery ligature for 45 minutes and the reperfusion for two hours, the infract size of cardiac injury areas could be reduced by orally administrating with the catechol-based derivatives after performing the coronary artery ligature for 15 minutes. The Table 15 and 16 show that the respective compounds 370G, 638J, 640, 638I, 642A, 642B, 639B, and 639C are capable of increasing the coronary flow rate. Therefore, it is suggested that the respective compounds 638J, 640, 638I, 642A, 642B, 639B, and 639C have the similar effect of the compound 370G for preventing the heart or other tissues damaging resulting from the myocardial infraction.

In view of the above experimental results, the catechol-based derivatives of the present invention are indeed capable of preventing or treating the diabetics and the ischaemic diseases and the implications thereof.

While the invention has been described with reference to the above examples, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for treating a diseases selected from type II diabetes or ischemia, comprising a step of administering to a subject in need thereof an effective amount of a pharmaceutical composition including a catechol-based derivative and a pharmaceutically acceptable carrier, wherein the catechol-based derivative is one of a compound of formula (Ia) or a pharmaceutically acceptable salt thereof:

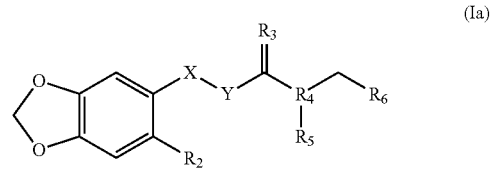

(Ia)

wherein $R_2$ is selected from the group consisting of H, —OR, —NO$_2$, —NH$_2$, and a halogen;
R in the —OR is one selected from the group consisting of H, ($C_1$-$C_6$)alkyl, (CH$_2$)$_n$Ph and SO$_3^-$;
$R_3$ is one of O and S;
$R_4$ is N;
X and Y form a structure being one selected from the group consisting of ($C_2$-$C_3$)alkyl, ($C_2$-$C_3$)alkenyl, ($C_2$-$C_3$)alkynyl, and —OCH$_2$—;
$R_5$ is one selected from the group consisting of H, $C_1$-$C_{15}$) alkyl, (CH$_2$)$_n$Ph and Ar, wherein the n is an integer from 1 to 3, and Ar is one selected from the group consisting of:

(g)

(h)

(i)

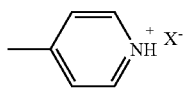
(j)

and a heteroaryl group;
$R_6$ is one of H and $(C_1-C_6)$ alkyl;
$R_7$, $R_8$, $R_9$ are selected from the group consisting of H, —OH, —OCH$_3$, —NO$_2$, —NH$_2$, —NH$_3^+$, and a halogen; and
$X^-$ represents one of an organic alkali and an inorganic alkali.

2. A method for treating a disease selected from type II diabetes or ischemia, comprising a step of administering to a subject in need thereof an effective amount of a pharmaceutical composition including a catechol-based derivative and a pharmaceutically acceptable carrier, wherein the catechol-based derivative is a compound of formula (I) and a pharmaceutically acceptable salt thereof:

(I)

wherein $R_1$ and $R_2$ are independently selected from the group consisting of H, —OR, —NO$_2$, —NH$_2$ and a halogen;
R in the —OR is one selected from the group consisting of H, $(C_1-C_6)$alkyl, $(CH_2)_n$Ph, and $SO_3^-$;
$R_3$ is one of O and S;
$R_4$ is N;
X and Y form a structure being one selected from the group consisting of $(C_2-C_3)$alkyl, $(C_2-C_3)$alkenyl, $(C_2-C_3)$alkynyl, and —OCH$_2$—;

$R_5$ is one selected from the group consisting of H, $(C_1-C_{15})$ alkyl, $(CH_2)_n$Ph and Ar, wherein the n is an integer from 1 to 3; and Ar is one selected from the group consisting of:

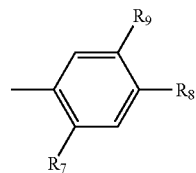
(g)

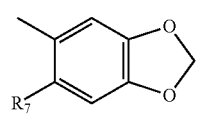
(h)

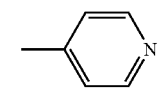
(i)

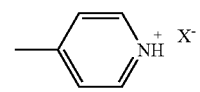
(j)

and a heteroaryl group;
$R_6$ is one of H and $(C_1-C_6)$ alkyl;
$R_7$, $R_8$, $R_9$ are selected from the group consisting of H, —OH, —OCH$_3$, —NO$_2$, —NH$_2$, —NH$_3^+$, and a halogen; and
$X^-$ represents one of an organic alkali and an inorganic alkali.

* * * * *